(12) United States Patent
Nelson et al.

(10) Patent No.: US 11,819,525 B2
(45) Date of Patent: Nov. 21, 2023

(54) MANAGEMENT OF PATHOGENIC LAWSONIA

(71) Applicant: Novozymes A/S, Bagsvaerd (DK)

(72) Inventors: Adam Nelson, Salem, VA (US); Erik Eckhardt, Domerat (FR); Estelle Devillard, Antony (FR); Meagan Hale, Roanoke, VA (US); Emily Zhang, Durham, NC (US); Ethan Chad Baker, Roanoke, VA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/933,582

(22) Filed: Sep. 20, 2022

(65) Prior Publication Data

US 2023/0138776 A1   May 4, 2023

Related U.S. Application Data

(62) Division of application No. 16/965,866, filed as application No. PCT/US2019/016271 on Feb. 1, 2019, now Pat. No. 11,478,514.

(60) Provisional application No. 62/625,549, filed on Feb. 2, 2018.

(51) Int. Cl.
| | |
|---|---|
| *A61K 35/742* | (2015.01) |
| *A23K 50/30* | (2016.01) |
| *A23K 10/18* | (2016.01) |
| *C12N 1/20* | (2006.01) |
| *C12R 1/10* | (2006.01) |
| *C12R 1/125* | (2006.01) |

(52) U.S. Cl.
CPC ............ *A61K 35/742* (2013.01); *A23K 10/18* (2016.05); *A23K 50/30* (2016.05); *C12N 1/205* (2021.05); *C12R 2001/10* (2021.05); *C12R 2001/125* (2021.05)

(58) Field of Classification Search
None
See application file for complete search history.

(56) References Cited

U.S. PATENT DOCUMENTS

| 8,227,235 B2 * | 7/2012 | Skinner | ............... A61K 35/742 |
|---|---|---|---|
| | | | 435/254.2 |
| 2010/0092428 A1 | 4/2010 | Schmidt | |
| 2010/0143417 A1 | 6/2010 | James | |
| 2018/0296475 A1 | 10/2018 | Sandvang | |

FOREIGN PATENT DOCUMENTS

| CN | 101418271 A | 4/2009 |
|---|---|---|
| WO | 2016118864 A1 | 7/2016 |
| WO | 2017012573 A1 | 1/2017 |
| WO | 2017/081105 A1 | 5/2017 |

OTHER PUBLICATIONS

Zeigler et al (J. Bacteriol. 190 (21), 6983-6995 (2008).*
Rey et al (Genome Biol. 5 (10), R77 (2004).*
Reva et a; (FEMS Microbiol. Ecol. 48 (2), 249-259. 2004).*
Opriessnig et al., 2019, Veterinary research, vol. 50, No. 85, pp. 1-11.
Yeh et al., 2011, Antimic Agents Chemoth , vol. 55, No. 9, pp. 4451-4453.
Jain et al., 2018, Nature Communications DOI:10.1038/s41467-018-07641-9, pp. 1-8.
Varghese et al., 2015, Nucelic Acids Research, vol. 43, No. 14, pp. 6761-6771.

* cited by examiner

*Primary Examiner* — Jennifer E Graser
(74) *Attorney, Agent, or Firm* — Adam Rucker

(57) ABSTRACT

The present invention relates to an animal feed or an animal feed additive comprising *Bacillus* strains which improve the health and performance of production animals, and the use of such.

20 Claims, 13 Drawing Sheets
Specification includes a Sequence Listing.

MANAGEMENT OF PATHOGENIC LAWSONIA

CROSS-REFERENCE TO RELATED APPLICATIONS

This application is a divisional application of U.S. application Ser. No. 16/965,866, filed Jul. 29, 2020 (now pending), which is a 35 U.S.C. 371 national application of international application no. PCT/US2019/016271, filed Feb. 1, 2019, and published as International Patent Application Publication WO2019/152791 on Aug. 8, 2019, which claims priority or the benefit under 35 U.S.C. 119 of U.S. provisional application No. 62/625,549, filed Feb. 2, 2018, the contents of each of which are fully incorporated herein by reference.

REFERENCE TO SEQUENCE LISTING

This application contains a Sequence Listing in computer readable form, which is incorporated herein by reference. The name of the file containing the Sequence Listing is SQ.XML, which was created on Sep. 20, 2022 and has 21.4 KB.
Index to sequence listing:
SEQ ID NO: 1 is 16S rDNA of DSM 32559
SEQ ID NO: 2 is 16S rDNA of DSM 32560
SEQ ID NO: 3 is 16S rDNA of DSM 32561
SEQ ID NO: 4 is 16S rDNA of DSM 32563
SEQ ID NO: 5 to SEQ ID NO: 10: PCR and sequencing primers
SEQ ID NO: 11 is 16S rDNA of O52YZ5
SEQ ID NO: 12 is 16S rDNA of O22FHD.

REFERENCE TO A DEPOSIT OF BIOLOGICAL MATERIAL

This application contains a reference to a deposit of biological material, which deposit is incorporated herein by reference. For complete information see last paragraph of the description.

FIELD OF THE INVENTION

The present invention relates to an animal feed or an animal feed additive comprising *Bacillus* strains which improve the health and performance of production animals. The invention further relates to use of the *Bacillus* strains in animal feed and animal feed additives.

BACKGROUND OF THE INVENTION

*Lawsonia intracellularis* (LI) is a bacterial pathogen causing the intestine disease proliferative enteropathy (PE) in a wide range of animals including pigs and horses. The pathogen is spread through the feces of the animals and causes diarrhea, depression, fever, inappetence (anorexia), weight loss, edema (fluid swelling) on the abdomen or lower limbs, a poor hair coat, and intermittent colic due to thickening of mucosal lining in the small and large intestine. Furthermore, chronic forms of PE may lead to clinical or sub-clinical effects on weight gain, feed conversion and fecal consistency. Clinical observations generally include diarrhea and poor Body Weight Gain of growing pigs.

Treatment of *Lawsonia intracellularis* infection is today limited to treatment with antibiotics. However, the treated animals do in many cases not recover fully after the treatment, and antibiotic resistance is sometimes experienced (Jung-Yong Yeh et al., Antimicrobial Agents and Chemotherapy, September 2011, p. 4451-4453).

An alternative to treatment with antibiotics is to vaccinate animals against infections induced by *Lawsonia intracellularis*. The purpose of a vaccination is to build up immunity in the animal before the first contact with the field pathogen. To get the best possible effect of a vaccine, animals must be vaccinated as early as possible, preferably in the first three weeks of life, to develop a reliable immunity before the first field infection.

There is a need for improved and sustainable methods for preventing and/or alleviating infections caused by *Lawsonia intracellularis*.

SUMMARY OF THE INVENTION

The invention provides *Bacillus* strains which have activity against *Lawsonia intracellularis* infection.

The invention further provides *Bacillus* strains having activity against *Lawsonia intracellularis* infection, wherein the strains reduce the number of heavily infected cells (HIC) in a method comprising the steps:
i) preparing a filtered cell-free extract comprising the *Bacillus* strain(s), Tryptic soy broth with yeast extract (TSBYE) and heat killed *E. coli*;
ii) from the extract of step i) preparing *Bacillus* supernatant dilutions comprising *Lawsonia intracellularis*;
iii) incubating the dilutions of step ii);
iv) adding the incubated dilutions of step iii) to murine fibroblast McCoy host cells;
v) incubating the host cells of step iv) to allow for *Lawsonia intracellularis* to infect the McCoy host cells;
vi) counting the number of heavily infected cells (HIC); and
vii) comparing the count from step vi) to the count of HIC in control cells prepared according to steps i) to v) but not comprising the *Bacillus* strains;
wherein the number of HIC is reduced at least 30% compared to the control cells.

In one aspect, body weight gain, average daily gain and/or feed conversion ratio is improved in animals which have been fed with the *Bacillus* strains of the invention. In one alternative or further aspect of the invention, the *Bacillus* strains reduce the effect of inflammation on Electrical Resistance in Caco-2 cells in vitro compared to the effect of inflammation on Electrical Resistance in Caco-2 cells in vitro without the *Bacillus* strain. In a further aspect, the effect of inflammation on Electrical Resistance is measured in a trans-epithelial electrical resistance (TEER) test.

The *Bacillus* strains of the invention decrease in further aspects the relative abundance of one or more members of the phylum Proteobacteria in the intestinal microbiome of animals fed with feed comprising the *Bacillus* strain.

In a yet further aspect, the *Bacillus* strains increase the relative abundance of one or more members of a specific genera selected from the group consisting of: *Ruminococcus, Blautia, Lactobacillus, Faecalibacterium*, and *Megasphera* in the intestinal microbiome of animals fed with feed comprising the *Bacillus* strain.

In a still further aspect of the invention, the *Bacillus* strains are selected from one or more *Bacillus subtilis* strains, one or more *Bacillus licheniformis* strains, one or more *Bacillus pumilus* strains, one or more *Bacillus amyloliquefaciens* strains, and any combination thereof.

The *Bacillus* strains according to the invention may prevent or alleviate *Lawsonia intracellularis* in production animals when fed to said animals. In one aspect, the production animals are selected from the group consisting of: pigs, swine, piglets, growing pigs, and sows.

In one aspect of the invention, the *Bacillus* strains of the invention may be in the form of spores. In a further aspect, at least 70% of the *Bacillus* spores survive the gastric environment in a swine such as e.g. pigs, piglets, growing pigs, or sows.

The invention also provides for compositions comprising one or more *Bacillus* strains described herein, the use of one or more *Bacillus* strains for prevention and/or alleviation of *Lawsonia intracellularis* in an animal, and animal feed or animal feed additives comprising one or more *Bacillus* strains described herein.

Also described herein is a method for improving one or more performance parameter(s) selected from the list consisting of body weight gain, average daily gain and feed conversion rate in an animal comprising the step of administering one or more *Bacillus* strains of the invention in the feed of the animal.

DEFINITIONS

Figure 1:
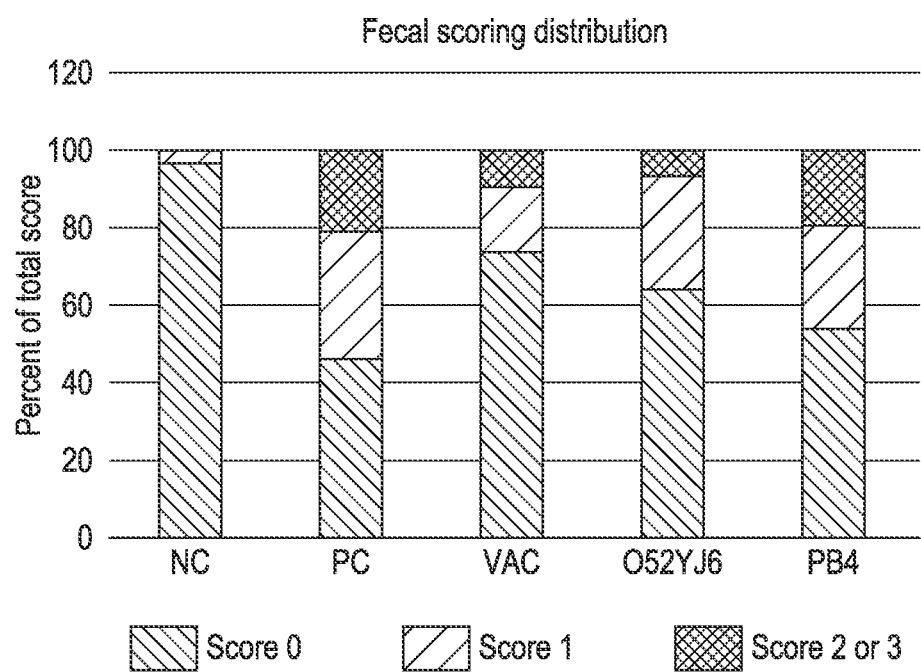
FIG. 1 shows the effect of feeding $1 \times 10^{12}$ CFU probiotics (O52YJ6 or 3002)/ton on average fecal scoring (score 0=best, i.e. no diarrhea) of animals during 21 days after an oral challenge with *Lawsonia intracellularis*.

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

Alleviate *Lawsonia intracellularis* infections: The term "alleviate *Lawsonia intracellularis* infections" means a method and/or composition that lightens or reduces development of a *Lawsonia intracellularis* infection in an animal.

Animal feed: The term "animal feed" refers to any compound, preparation, or mixture suitable for, or intended for intake by an animal. Animal feed for a production animal comprises concentrates as well as for example vitamins, minerals, enzymes, amino acids and/or other feed ingredients (such as in a premix). The animal feed may further comprise forage.

Average Daily Gain: The Average Daily Gain (ADG) of an animal is the increase in bodyweight of the animal per day expressed in g/day. Typically the weight of the animal is measured at a few time points during the experiment and the difference in weight is then divided by the number of days in the measured period to get the Average Daily Gain. An example of Average Daily Gain determination is given in Example 4.

Blend: the term "blend" means more than one of the bacterial strains described herein.

Body Weight Gain: The Body Weight Gain of an animal is the increase of body weight of the animal over a specified time period. The body weight gain can readily be determined by weighing the animal at two timepoints and calculating the gain in weight by subtracting the weight at the first timepoint from the weight at the second timepoint.

Composition: The term "composition" refers to a composition comprising a carrier and at least one bacterial strain as described herein. The compositions described herein may be mixed with an animal feed(s) to obtain a "mash feed", extruded or pressed feed pellets, or liquid feed.

Concentrates: The term "concentrates" means feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Direct Fed Microbial (DFM): The term "direct fed microbial" or "DFM" means live micro-organisms including spores which, when administered in adequate amounts, confer a benefit, such as improved digestion or health, on the host.

Effective amount/concentration/dosage: The terms "effective amount", "effective concentration", or "effective dosage" are defined as the amount, concentration, or dosage of the bacterial strain(s) sufficient to improve the digestion or yield of an animal. The actual effective dosage in absolute numbers depends on factors including: the state of health of the animal in question, other ingredients, additives, or drugs present. The "effective amount", "effective concentration", or "effective dosage" of the bacterial strains may be determined by routine assays known to those skilled in the art.

Fed: The term "fed" means any type of oral administration such as administration via an animal feed or via drinking water.

FCR (Feed Conversion Rate): FCR is a measure of an animal's efficiency in converting feed mass into increases of the desired output, where the output is the mass gained by the animal. The term is used for animals that are raised for meat, such as e.g. swine, poultry and fish. Specifically, FCR is the mass of the food eaten divided by the output, all over a specified period. Improvement in FCR means reduction of the FCR value. A FCR improvement of 2% means that the FCR was reduced by 2%.

Feeding an animal: The terms "feeding an animal" or "fed to an animal" means that the composition of the present invention is administered orally to the animal one or more times in an effective amount. The oral administration is typically repeated, e.g., one or more times daily over a specified time period such as several days, one week, several weeks, one months or several months. Accordingly, the terms "feeding" or "fed" mean any type of oral administration such as administration via an animal feed or via drinking water.

Survive the gastric environment: The term "survive the gastric environment" is herein used for describing the ability of e.g. a *Bacillus* spore to survive in an environment mimicking the environment in the gastrointestinal tract in vitro. The ability to survive the gastric environment may be measured according to methods generally known in the art. In one embodiment, the ability to survive the gastric environment is measured as described in T. M. Barbosa, C. R. Serra, R. M. La Ragione, M. J. Woodward, A. O. Henriques. Screening for *Bacillus* isolates in the broiler gastrointestinal tract. Appl. Environ. Microbiol., 71 (2005), pp. 968-978.

IgG score: The term "IgG score" indicates to what extent immunoglobulin G directed against *Lawsonia intracellularis* was produced in response to an infection with *Lawsonia intracellularis*. A low IgG score indicates a limited infection with low morbidity, whereas a high score indicates a severe infection with higher risk of intestinal lesion formation and other morbidity.

Isolated: The term "isolated" means that the one or more bacterial strains described herein are in a form or environment which does not occur in nature, that is, the one or more bacterial strains are at least partially removed from one or more or all of the naturally occurring constituents with which it is associated in nature.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Premix: The term is used for a mixture of micro ingredients such as e.g. vitamins, minerals, enzymes, amino acids, preservatives, antibiotics, other feed ingredients or any combination thereof, and typically exists as a powder or in granulate form. The premix is mixed into the animal feed before feeding to animals. This is opposed to e.g. macro ingredients such as cereals which are usually added separately to the animal feed.

Prevent *Lawsonia intracellularis* infections: The term "prevent *Lawsonia intracellularis* infections" means a method and/or composition that prevents and/or controls development of a *Lawsonia intracellularis* infection in an animal.

Relative abundance: The term "relative abundance" when used in connection with the intestinal microbiome of animals indicates the proportion of sequences matching a known and identified taxonomic group in a sample, compared to all sequences from that sample.

Spore: The terms "spore" and "endospore" are interchangeable and have their normal meaning which is well known and understood by those of skill in the art. As used herein, the term spore refers to a microorganism in its dormant, protected state.

Stable: The term "stable" is a term that is known in the art, and in a preferred aspect, stable is intended to mean the ability of the microorganism to remain in a spore form until it is administered to an animal to improve the health of the animal.

Swine: The term "swine" or "pigs" means domesticated pigs kept by humans for food, such as their meat. Swine includes members of the genus *Sus*, such as *Sus scrofa domesticus* or *Sus domesticus* and include piglets, growing pigs, sows, and boars.

TEER (Trans-Epithelial Electrical Resistance): The term "TEER" means Trans-Epithelial Electrical Resistance. It is a measure of the electrical resistance across a cell membrane and gives an indication of tight junctions or barrier function. TEER is generally used as an in vitro model for the strength of the intestinal barrier function. The greater the electrical resistance, the stronger the barrier function.

Vegetable protein: The term "vegetable protein" refers to any compound, preparation or mixture that includes at least one protein derived from or originating from a vegetable, including modified proteins and protein-derivatives.

DETAILED DESCRIPTION OF THE INVENTION

The present invention includes methods of alleviating and/or treating an animal against infection by *Lawsonia intracellularis* or similar or otherwise related microorganisms, and/or methods of preventing against infection by *Lawsonia intracellularis* or similar or otherwise related microorganisms in an animal. The method includes administering one or more *Bacillus* strains to the animal in a dose sufficient to alleviate, treat and/or prevent *Lawsonia intracellularis* infection.

It has been surprisingly found that the addition of direct fed microbes (DFM) from *Bacillus* species to animal feed can be used to prevent, alleviate and/or treat *Lawsonia intracellularis* infections in production animals such as pigs and/or poultry and at the same time improve the body weight gain (BWG), average daily gain (ADG) and/or feed conversion ratio (FCR) (in both *Lawsonia intracellularis* challenged and unchallenged animals). Further, it was surprisingly found that *Bacillus* strains may further reduce the effect of inflammation on Electrical Resistance in Caco-2 cells in vitro and/or decrease the relative abundance of one or more members of the phylum Proteobacteria in the intestinal microbiome of animals fed with feed comprising the *Bacillus* strain and/or increase the relative abundance of one or more members of a specific genera selected from the group consisting of: *Ruminococcus, Blautia, Lactobacillus, Faecalibacterium* and *Megasphera* in the intestinal microbiome of animals fed with feed comprising the *Bacillus* strain.

The inventors have identified *Bacillus* strains which are active against the pathogen *Lawsonia intracellularis*.

It has furthermore surprisingly been found that when using the *Bacillus* strains of the invention, the ability of *Lawsonia intracellularis* to cause re-infection of swine is reduced.

In one embodiment, the *Bacillus* strains described herein decrease the shedding of *Lawsonia intracellularis* organisms in the feces, and/or reduce or decrease the number of gross lesions in intestinal tissue at necropsy.

In one embodiment, the risk of developing severe diarrhea upon challenge with *Lawsonia intracellularis* may be indicated by determining the fecal consistency using fecal scoring. Fecal consistency is primarily a function of the amount of moisture in the stool and can be used to identify changes in colonic health and other problems. Ideally, in a healthy animal, stools should be firm but not hard, pliable and segmented, and easy to pick up (i.e. score 0 in example 2).

The invention relates to the following aspects and embodiments with respect to *Bacillus* strains:

Aspect 1: One or more *Bacillus* strains characterized in that:
 i) the *Bacillus* strain has activity against a *Lawsonia intracellularis* infection, and
 ii) the *Bacillus* strain improves body weight gain (BWG) and/or average daily gain (ADG) and/or feed conversion ratio (FCR) in animals fed with the *Bacillus* strain.

Aspect 2: One or more *Bacillus* strains having activity against *Lawsonia intracellularis* infection, wherein the strains reduce the number of heavily infected cells (HIC) in a method comprising the steps:

i) preparing a filtered cell-free extract comprising the *Bacillus* strain(s), Tryptic soy broth with yeast extract (TSBYE) and heat killed *E. coli*;
 ii) from the extract of step i) preparing *Bacillus* supernatant dilutions comprising *Lawsonia intracellularis*;
 iii) incubating the dilutions of step ii);
 iv) adding the incubated dilutions of step iii) to murine fibroblast McCoy host cells;
 v) incubating the host cells of step iv) to allow for *Lawsonia intracellularis* to infect the McCoy host cells;
 vi) counting the number of heavily infected cells (HIC); and
 vii) comparing the count from step vi) to the count of HIC in control cells prepared according to steps i) to v) but not comprising the *Bacillus* strains;
 wherein the number of HIC is reduced at least 30% compared to the control cells.

In one embodiment, the *Bacillus* strain of the invention reduces the effect of inflammation on Electrical Resistance in Caco-2 cells in vitro compared to the effect of inflammation on Electrical Resistance in Caco-2 cells in vitro without the *Bacillus* strain. In one particular embodiment, the effect of inflammation on Electrical Resistance is measured in a trans-epithelial electrical resistance (TEER) test.

In one embodiment, the *Bacillus* strain decreases the relative abundance of one or more members of the phylum Proteobacteria in the intestinal microbiome of animals fed with feed comprising the *Bacillus* strain compared to animals fed with the same feed without the *Bacillus* strain. The members of the phylum Proteobacteria are in one embodiment selected from the group consisting of: *Escherichia, Shigella, Campylobacter, Burkholderia, Acinetobacter* and any combination thereof.

In one embodiment, the *Bacillus* strain increases the relative abundance of one or more members of a specific genera selected from the group consisting of: *Ruminococcus, Blautia, Lactobacillus, Faecalibacterium*, and *Megasphera* in the intestinal microbiome of animals fed with feed comprising the *Bacillus* strain compared to animals fed with the same feed without the *Bacillus* strain.

In one embodiment the improvement in body weight gain results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as explained in the definition of body weight gain.

In one embodiment the improvement in average daily gain results in an average daily gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in average daily gain for results in an average daily gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The average daily gain can be determined as described in Example 4.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 1.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 2.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 3.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 4.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 11.

In one embodiment of the invention, the *Bacillus* strain comprises 16S rDNA that is more than 98% (such as more than 98.5%, such as more than 99%, such as more than 99.5%, such as more than 99.5%) sequence identity to SEQ ID NO: 12.

In one embodiment, the one or more *Bacillus* strains of the invention are selected from the group consisting of:
 a. *Bacillus licheniformis* strain O42AH3 having deposit accession number DSM 32559 or a strain having all the identifying characteristics of *Bacillus licheniformis* strain DSM 32559 or a mutant thereof,
 b. *Bacillus subtilis* strain O52YJ6 having deposit accession number DSM 32560 or a strain having all the identifying characteristics of *Bacillus subtilis* strain DSM 32560 or a mutant thereof,
 c. *Bacillus amyloliquefaciens* strain O52YYT having deposit accession number DSM 32561 or a strain having all the identifying characteristics of *Bacillus amyloliquefaciens* strain DSM 32561 or a mutant thereof,
 d. *Bacillus pumilus* strain O72NR7 having deposit accession number DSM 32563 or a strain having all the identifying characteristics of *Bacillus pumilus* strain DSM 32563 or a mutant thereof, and
 e. *Bacillus subtilis* strain SB3175 having deposit accession number NRRL B-50605 or a strain having all the identifying characteristics of *Bacillus subtilis* strain NRRL B-50605 or a mutant thereof.

In one embodiment, the one or more *Bacillus* strains of the invention are selected from the group consisting of:
 a. *Bacillus licheniformis* strain O42AH3 having deposit accession number DSM 32559 or a strain having all the identifying characteristics of *Bacillus licheniformis* strain DSM 32559 or a mutant thereof,
 b. *Bacillus subtilis* strain O52YJ6 having deposit accession number DSM 32560 or a strain having all the identifying characteristics of *Bacillus subtilis* strain DSM 32560 or a mutant thereof,
 c. *Bacillus amyloliquefaciens* strain O52YYT having deposit accession number DSM 32561 or a strain having all the identifying characteristics of *Bacillus amyloliquefaciens* strain DSM 32561 or a mutant thereof, and
 d. *Bacillus pumilus* strain O72NR7 having deposit accession number DSM 32563 or a strain having all the identifying characteristics of *Bacillus pumilus* strain DSM 32563 or a mutant thereof.

In one embodiment, the one or more *Bacillus* strains of the invention are selected from the group consisting of:
 a. *Bacillus amyloliquefaciens* strain O52YYT having deposit accession number DSM 32561 or a strain having all the identifying characteristics of *Bacillus amyloliquefaciens* strain DSM 32561 or a mutant thereof, and
 b. *Bacillus pumilus* strain O72NR7 having deposit accession number DSM 32563 or a strain having all the identifying characteristics of *Bacillus pumilus* strain DSM 32563 or a mutant thereof.

In one embodiment, the *Bacillus* strain of the invention is *Bacillus amyloliquefaciens* strain O52YYT having deposit accession number DSM 32561 or a strain having all the identifying characteristics of *Bacillus amyloliquefaciens* strain DSM 32561 or a mutant thereof.

In one embodiment, the *Bacillus* strain of the invention is *Bacillus pumilus* strain O72NR7 having deposit accession number DSM 32563 or a strain having all the identifying characteristics of *Bacillus pumilus* strain DSM 32563 or a mutant thereof.

In one embodiment, the invention relates to a composition comprising spores of one or more *Bacillus* strains according to invention.

More specifically the invention relates to the following aspects and embodiments with respect to compositions comprising *Bacillus* strains:

Aspect 3: A composition comprising spores of a *Bacillus* strain characterized in that:
 i) the *Bacillus* strain has activity against an *Lawsonia intracellularis* infection, and ii) the *Bacillus* strain improves body weight gain (BWG) and/or average daily gain (ADG) and/or feed conversion ratio (FCR) in animals fed with the *Bacillus* strain.

Aspect 4: A composition comprising spores of a *Bacillus* strains having activity against *Lawsonia intracellularis* infection, wherein the strains reduce the number of heavily infected cells (HIC) in a method comprising the steps:
 i) preparing a filtered cell-free extract comprising the *Bacillus* strain(s), Tryptic soy broth with yeast extract (TSBYE) and heat killed *E. coli;*
 ii) from the extract of step i) preparing *Bacillus* supernatant dilutions comprising *Lawsonia intracellularis;*
 iii) incubating the dilutions of step ii);
 iv) adding the incubated dilutions of step iii) to murine fibroblast McCoy host cells;
 v) incubating the host cells of step iv) to allow for *Lawsonia intracellularis* to infect the McCoy host cells;
 vi) counting the number of heavily infected cells (HIC); and
 vii) comparing the count from step vi) to the count of HIC in control cells prepared according to steps i) to v) but not comprising the *Bacillus* strains;
 wherein the number of HIC is reduced at least 30% compared to the control cells.

In one embodiment of the invention, the *Bacillus* strain of the composition reduces the effect of inflammation on Electrical Resistance in Caco-2 cells in vitro compared to the effect of inflammation on Electrical Resistance in Caco-2 cells in vitro without the *Bacillus* strain. In one particular embodiment, the effect of inflammation on Electrical Resistance is measured in a trans-epithelial electrical resistance (TEER) test.

In one embodiment of the invention, the *Bacillus* strain of the composition decreases the relative abundance of one or more members of the phylum Proteobacteria in the intestinal microbiome of animals fed with feed comprising the *Bacillus* strain compared to animals fed with the same feed without the *Bacillus* strain. The members of the phylum Proteobacteria are in one embodiment selected from the group consisting of: *Escherichia, Shigella, Campylobacter, Burkholderia, Acinetobacter* and any combination thereof.

In one embodiment of the invention, the *Bacillus* strain of the composition increases the relative abundance of one or more members of a specific genera selected from the group consisting of: *Ruminococcus, Blautia, Lactobacillus, Faecalibacterium*, and *Megasphera* in the intestinal microbiome of animals fed with feed comprising the *Bacillus* strain compared to animals fed with the same feed without the *Bacillus* strain.

In one embodiment the improvement in body weight gain results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as explained in the definition of body weight gain.

In one embodiment the improvement in food conversion rate results in a food conversion rate improvement of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment, the improvement in food conversion rate results in a food conversion rate improvement selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The food conversion rate can be determined as explained in the definition of food conversion rate.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 1.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 2.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 3.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 4.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 11.

In one embodiment of the invention, the *Bacillus* strain of the composition comprises 16S rDNA that is more than 98% (such as more than 98.5%, such as more than 99%, such as more than 99.5%, such as more than 99.5%) sequence identity to SEQ ID NO: 12.

In one embodiment of the invention the *bacillus* spores of the composition are present as dried spores such as spray-dried spores. In one embodiment of the invention the *bacillus* spores of the composition are present as stable spores. The composition according to the invention can also be a liquid composition and/or comprise culture supernatant comprising one or more *Bacillus* strain(s) of the invention.

In one embodiment of the invention the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose farigel, cassava cores, sodium aluminium silicate, colloidal amorphous silica, Sipernat 505, polyethylene glycol 200, polyethylene glycol 400, polyethylene glycol 600, polyethylene glycol 1000, polyethylene glycol 1500, polyethylene glycol 4000 and carbopol.

In a preferred embodiment of the invention the composition further comprises calcium carbonate and sodium aluminium silicate.

In a preferred embodiment of the invention the composition further comprises calcium carbonate, sodium aluminium silicate and sucrose.

In another preferred embodiment of the invention the composition further comprises one or more carriers such as one or more carriers selected from the group consisting of Calcium carbonate, sodium sulfate, starch, farigel and cassava cores.

In another preferred embodiment of the invention the composition further comprises one or more flowability agents such as sodium aluminium silicate and/or colloidal amorphous silica (e.g., Sipernat 50S).

In another preferred embodiment of the invention the composition further comprises one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus licheniformis* strain O42AH3 having deposit accession number DSM 32559 or a strain having all the identifying characteristics of *Bacillus licheniformis* strain DSM 32559 or a mutant thereof, calcium carbonate and sodium aluminium silicate.

In a preferred embodiment the composition comprises *Bacillus licheniformis* strain O42AH3 having deposit accession number DSM 32559 or a strain having all the identifying characteristics of *Bacillus licheniformis* strain DSM 32559 or a mutant thereof, calcium carbonate, sodium aluminium silicate and sucrose.

In a preferred embodiment the composition comprises *Bacillus licheniformis* strain O42AH3 having deposit accession number DSM 32559 or a strain having all the identifying characteristics of *Bacillus licheniformis* strain DSM 32559 or a mutant thereof and one or more carriers such as one or more carriers selected from the group consisting of calcium carbonate, sodium sulphate, starch, farigel and cassava cores.

In a preferred embodiment the composition comprises *Bacillus licheniformis* strain O42AH3 having deposit accession number DSM 32559 or a strain having all the identifying characteristics of *Bacillus licheniformis* strain DSM 32559 or a mutant thereof and one or more flowability agents such as sodium aluminium silicate and/or colloidal amorphous silica (e.g., Sipernat 50S).

In a preferred embodiment the composition comprises *Bacillus licheniformis* strain O42AH3 having deposit accession number DSM 32559 or a strain having all the identifying characteristics of *Bacillus licheniformis* strain DSM 32559 or a mutant thereof and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus pumilus* strain O72NR7 having deposit accession number DSM 32563 or a strain having all the identifying characteristics of *Bacillus pumilus* strain DSM 32563 or a mutant thereof, calcium carbonate and sodium aluminium silicate.

In a preferred embodiment the composition comprises *Bacillus pumilus* strain O72NR7 having deposit accession number DSM 32563 or a strain having all the identifying characteristics of *Bacillus pumilus* strain DSM 32563 or a mutant thereof, calcium carbonate, sodium aluminium silicate and sucrose.

In a preferred embodiment the composition comprises *Bacillus pumilus* strain O72NR7 having deposit accession number DSM 32563 or a strain having all the identifying characteristics of *Bacillus pumilus* strain DSM 32563 or a mutant thereof and one or more carriers such as one or more carriers selected from the group consisting of calcium carbonate, sodium sulphate, starch, farigel and cassava cores.

In a preferred embodiment the composition comprises *Bacillus pumilus* strain O72NR7 having deposit accession number DSM 32563 or a strain having all the identifying characteristics of *Bacillus pumilus* strain DSM 32563 or a mutant thereof and one or more flowability agents such as sodium aluminium silicate and/or colloidal amorphous silica (e.g., Sipernat 50S).

In a preferred embodiment the composition comprises *Bacillus pumilus* strain O72NR7 having deposit accession number DSM 32563 or a strain having all the identifying characteristics of *Bacillus pumilus* strain DSM 32563 or a mutant thereof and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus amyloliquefaciens* strain O52YYT having deposit accession number DSM 32561 or a strain having all the identifying characteristics of *Bacillus amyloliquefaciens* strain DSM 32561 or a mutant thereof, calcium carbonate and sodium aluminium silicate.

In a preferred embodiment the composition comprises *Bacillus amyloliquefaciens* strain O52YYT having deposit accession number DSM 32561 or a strain having all the identifying characteristics of *Bacillus amyloliquefaciens* strain DSM 32561 or a mutant thereof, calcium carbonate, sodium aluminium silicate and sucrose.

In a preferred embodiment the composition comprises *Bacillus amyloliquefaciens* strain O52YYT having deposit accession number DSM 32561 or a strain having all the identifying characteristics of *Bacillus amyloliquefaciens* strain DSM 32561 or a mutant thereof and one or more carriers such as one or more carriers selected from the group consisting of calcium carbonate, sodium sulphate, starch, farigel and cassava cores.

In a preferred embodiment the composition comprises *Bacillus amyloliquefaciens* strain O52YYT having deposit accession number DSM 32561 or a strain having all the identifying characteristics of *Bacillus amyloliquefaciens* strain DSM 32561 or a mutant thereof and one or more flowability agents such as sodium aluminium silicate and/or colloidal amorphous silica (e.g., Sipernat 50S).

In a preferred embodiment the composition comprises *Bacillus amyloliquefaciens* strain O52YYT having deposit accession number DSM 32561 or a strain having all the identifying characteristics of *Bacillus amyloliquefaciens* strain DSM 32561 or a mutant thereof and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition according to the invention the composition comprises from $10^4$ to $10^{14}$ CFU/g of isolated *Bacillus* spores In a further embodiment, the composition according to the invention comprises one or more bacterial strains such as at least two of the above strains up to and including all of the strains in the group consisting of:
a. *Bacillus licheniformis* strain O42AH3 having deposit accession number DSM 32559 or a strain having all the identifying characteristics of *Bacillus licheniformis* strain DSM 32559 or a mutant thereof,
b. *Bacillus subtilis* strain O52YJ6 having deposit accession number DSM 32560 or a strain having all the identifying characteristics of *Bacillus subtilis* strain DSM 32560 or a mutant thereof,
c. *Bacillus amyloliquefaciens* strain O52YYT having deposit accession number DSM 32561 or a strain having all the identifying characteristics of *Bacillus amyloliquefaciens* strain DSM 32561 or a mutant thereof,
d. *Bacillus pumilus* strain O72NR7 having deposit accession number DSM 32563 or a strain having all the identifying characteristics of *Bacillus pumilus* strain DSM 32563 or a mutant thereof, and
e. *Bacillus subtilis* strain SB3175 having deposit accession number NRRL B-50605 or a strain having all the identifying characteristics of *Bacillus subtilis* strain NRRL B-50605 or a mutant thereof.

In a further embodiment, the composition according to the invention comprises one or more bacterial strains such as at least two of the above strains up to and including all of the strains in the group consisting of:
  a. *Bacillus licheniformis* strain O42AH3 having deposit accession number DSM 32559 or a strain having all the identifying characteristics of *Bacillus licheniformis* strain DSM 32559 or a mutant thereof,
  b. *Bacillus subtilis* strain O52YJ6 having deposit accession number DSM 32560 or a strain having all the identifying characteristics of *Bacillus subtilis* strain DSM 32560 or a mutant thereof,
  c. *Bacillus amyloliquefaciens* strain O52YYT having deposit accession number DSM 32561 or a strain having all the identifying characteristics of *Bacillus amyloliquefaciens* strain DSM 32561 or a mutant thereof, and
  d. *Bacillus pumilus* strain O72NR7 having deposit accession number DSM 32563 or a strain having all the identifying characteristics of *Bacillus pumilus* strain DSM 32563 or a mutant thereof.

In a further embodiment, the composition according to the invention comprises one or more bacterial strains such as at least two of the above strains up to and including all of the strains in the group consisting of:
  a. *Bacillus amyloliquefaciens* strain O52YYT having deposit accession number DSM 32561 or a strain having all the identifying characteristics of *Bacillus amyloliquefaciens* strain DSM 32561 or a mutant thereof, and
  b. *Bacillus pumilus* strain O72NR7 having deposit accession number DSM 32563 or a strain having all the identifying characteristics of *Bacillus pumilus* strain DSM 32563 or a mutant thereof.

In an embodiment to any of the aforementioned embodiments, development of severe diarrhea is prevented after 24 hours, such as after 36 hours, 2 days, 3 days, 4 days, 5 days, 6 days or 1 week of feeding the *Bacillus* spore to the animal.

In another embodiment to any of the aforementioned embodiments, development of severe diarrhea is prevented after 2 weeks, such as after 3 weeks, 4 weeks, 1 month, 2 months, 3 months, 4 months, 5 months, 6 months or 1 year of feeding the *Bacillus* spore to the animal.

In an embodiment to any of the aforementioned embodiments, shedding of *Lawsonia intracellularis* in feces is decreased for animals fed with the *Bacillus* spore compared to animals not fed with *Bacillus* strains.

In a further embodiment, shedding of *Lawsonia intracellularis* in feces is decreased after feeding the *Bacillus* spore to the animal for at least 24 hours, such as at least 36 hours, 2 days, 3 days, 4 days, 5 days, 6 days or 1 week.

In another embodiment to any of the aforementioned embodiments, shedding of *Lawsonia intracellularis* in feces is decreased after feeding the *Bacillus* spore to the animal for at least 2 weeks, such as at least 3 weeks, 4 weeks, 1 month, 2 months, 3 months, 4 months, 5 months, 6 months or 1 year.

In an embodiment to any of the aforementioned embodiments, lesions in the intestinal tract of the animal are reduced after feeding the *Bacillus* strain to the animal for at least 24 hours, such as at least 36 hours, 2 days, 3 days, 4 days, 5 days, 6 days or 1 week compared to lesions in the intestinal tract of an animal not fed with *Bacillus* strains.

In another embodiment to any of the aforementioned embodiments, lesions in the intestinal tract of the animal are reduced after feeding the *Bacillus* strain to the animal for at least 2 weeks, such as at least 3 weeks, 4 weeks, 1 month, 2 months, 3 months, 4 months, 5 months, 6 months or 1 year compared to lesions in the intestinal tract of an animal not fed with *Bacillus* strains.

In an embodiment to any of the aforementioned embodiments, the IgG score in the animal is reduced after feeding the *Bacillus* strain to the animal for at least 24 hours, such as at least 36 hours, 2 days, 3 days, 4 days, 5 days, 6 days or 1 week compared to the IgG score in animals not fed with *Bacillus* strains.

In another embodiment to any of the aforementioned embodiments, the IgG score in the animal is reduced after feeding the *Bacillus* strain to the animal for at least 2 weeks, such as at least 3 weeks, 4 weeks, 1 month, 2 months, 3 months, 4 months, 5 months, 6 months or 1 year compared to the IgG score in animals not fed with *Bacillus* strains.

In an embodiment to any of the aforementioned embodiments, Average Daily Gain of the animal is increased after feeding the *Bacillus* strain to the animal for at least 24 hours, such as at least 36 hours, 2 days, 3 days, 4 days, 5 days, 6 days or 1 week compared to the Average Daily Gain of animals not fed with *Bacillus* strains.

In another embodiment to any of the aforementioned embodiments, Average Daily Gain of the animal is increased after feeding the *Bacillus* strain to the animal for at least 2 weeks, such as at least 3 weeks, 4 weeks, 1 month, 2 months, 3 months, 4 months, 5 months, 6 months or 1 year compared to the Average Daily Gain of animals not fed with *Bacillus* strains.

In an embodiment to any of the aforementioned embodiments, Feed Conversion Rate (FCR) of the animal is improved after feeding the *Bacillus* strain to the animal for at least 24 hours, such as at least 36 hours, 2 days, 3 days, 4 days, 5 days, 6 days or 1 week compared to the Average Daily Gain of animals not fed with *Bacillus* strains.

In another embodiment to any of the aforementioned embodiments, Feed Conversion Rate (FCR) of the animal is improved after feeding the *Bacillus* strain to the animal for at least 2 weeks, such as at least 3 weeks, 4 weeks, 1 month, 2 months, 3 months, 4 months, 5 months, 6 months or 1 year compared to the Average Daily Gain of animals not fed with *Bacillus* strains.

In an embodiment to any of the aforementioned embodiments, the risk of developing Proliferative Hemorrhagic Enteropathy (PHE) is reduced after 24 hours, such as after 36 hours, 2 days, 3 days, 4 days, 5 days, 6 days or 1 week of feeding the *Bacillus* spore to the animal.

In another embodiment to any of the aforementioned embodiments, the risk of developing Proliferative Hemorrhagic Enteropathy (PHE) is reduced after 2 weeks, such as after 3 weeks, 4 weeks, 1 month, 2 months, 3 months, 4 months, 5 months, 6 months or 1 year of feeding the *Bacillus* spore to the animal.

In another embodiment of the invention the composition further comprises one or more additional microbes. In another embodiment of the invention the composition further comprises one or more additional vaccines such as e.g. Enterisol. In another embodiment of the invention the composition further comprises one or more enzymes. In another embodiment of the invention the composition further comprises one or more vitamins. In another embodiment of the invention the composition further comprises one or more minerals. In another embodiment of the invention the composition further comprises one or more amino acids. In another embodiment of the invention the composition further comprises one or more other feed ingredients.

In an embodiment to any of the aforementioned embodiments, the composition also improves the health of the production animal when fed to said animal. In an embodiment to any of the aforementioned embodiments, the composition increases the meat yield of the production animal when fed to said animal.

In a preferred embodiment, the composition comprises one or more bacterial strains described herein, wherein the bacterial count of each of the bacterial strains is between $1 \times 10^4$ and $1 \times 10^{12}$ CFU/kg of composition, preferably between $1 \times 10^7$ and $1 \times 10^{11}$ CFU/kg of composition, more preferably between $1 \times 10^8$ and $1 \times 10^{10}$ CFU/kg of composition and most preferably between $1 \times 10^9$ and $1 \times 10^{10}$ CFU/kg of composition.

In a preferred embodiment, the bacterial count of each of the bacterial strains in the composition is between $1 \times 10^4$ and $1 \times 10^{12}$ CFU/kg of dry matter, preferably between $1 \times 10^7$ and $1 \times 10^{11}$ CFU/kg of dry matter, more preferably between $1 \times 10^8$ and $1 \times 10^{11}$ CFU/kg of dry matter and most preferably between $1 \times 10^8$ and $1 \times 10^{10}$ CFU/kg of dry matter. In a more preferred embodiment the bacterial count of each of the bacterial strains in the composition is between $1 \times 10^9$ and $1 \times 10^{10}$ CFU/kg of dry matter In a preferred embodiment, the composition has a bacterial count of each *Bacillus* spore between $1 \times 10^3$ and $1 \times 10^{13}$ CFU/animal/day, preferably between $1 \times 10^5$ and $1 \times 10^{11}$ CFU/animal/day, more preferably between $1 \times 10^6$ and $1 \times 10^{10}$ CFU/animal/day and most preferably between $1 \times 10^7$ and $1 \times 10^9$ CFU/animal/day.

In still yet another embodiment of the invention, the one or more bacterial strains are present in the composition in form of a spore such as a stable spore. In still a further embodiment of the invention, the stable spore will germinate in the intestine and/or stomach of the mono-gastric animal.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar, particularly 10 bar to 40 bar, more particularly 15 bar to 40 bar, even more particularly 20 bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 60° C. to 120° C., particularly temperatures ranging from, 90° C. to 120° C., even more particularly temperatures ranging from 95° C. to 120° C.

In another aspect, the invention relates to a composition comprising a carrier and one or more of the bacteria cultures having characteristics substantially identical to that of a strain selected from the group consisting of:
  a. *Bacillus licheniformis* strain O42AH3 having deposit accession number DSM 32559 or a strain having all the identifying characteristics of *Bacillus licheniformis* strain DSM 32559 or a mutant thereof,
  b. *Bacillus subtilis* strain O52YJ6 having deposit accession number DSM 32560 or a strain having all the identifying characteristics of *Bacillus subtilis* strain DSM 32560 or a mutant thereof,
  c. *Bacillus amyloliquefaciens* strain O52YYT having deposit accession number DSM 32561 or a strain having all the identifying characteristics of *Bacillus amyloliquefaciens* strain DSM 32561 or a mutant thereof,
  d. *Bacillus pumilus* strain O72NR7 having deposit accession number DSM 32563 or a strain having all the identifying characteristics of *Bacillus pumilus* strain DSM 32563 or a mutant thereof, and
  e. *Bacillus subtilis* strain SB3175 having deposit accession number NRRL B-50605 or a strain having all the identifying characteristics of *Bacillus subtilis* strain NRRL B-50605 or a mutant thereof.

In another aspect, the invention relates to a composition comprising a carrier and one or more of the bacteria cultures having characteristics substantially identical to that of a strain selected from the group consisting of:
  a. *Bacillus licheniformis* strain O42AH3 having deposit accession number DSM 32559 or a strain having all the identifying characteristics of *Bacillus licheniformis* strain DSM 32559 or a mutant thereof,
  b. *Bacillus subtilis* strain O52YJ6 having deposit accession number DSM 32560 or a strain having all the identifying characteristics of *Bacillus subtilis* strain DSM 32560 or a mutant thereof,
  c. *Bacillus amyloliquefaciens* strain O52YYT having deposit accession number DSM 32561 or a strain having all the identifying characteristics of *Bacillus amyloliquefaciens* strain DSM 32561 or a mutant thereof, and
  d. *Bacillus pumilus* strain O72NR7 having deposit accession number DSM 32563 or a strain having all the identifying characteristics of *Bacillus pumilus* strain DSM 32563 or a mutant thereof.

In another aspect, the invention relates to a composition comprising a carrier and one or more of the bacteria cultures having characteristics substantially identical to that of a strain selected from the group consisting of:
  a. *Bacillus amyloliquefaciens* strain O52YYT having deposit accession number DSM 32561 or a strain having all the identifying characteristics of *Bacillus amyloliquefaciens* strain DSM 32561 or a mutant thereof, and
  b. *Bacillus pumilus* strain O72NR7 having deposit accession number DSM 32563 or a strain having all the identifying characteristics of *Bacillus pumilus* strain DSM 32563 or a mutant thereof.

In another aspect, the invention relates to a composition comprising a carrier and one or more of the bacteria cultures having characteristics substantially identical to that of *Bacillus amyloliquefaciens* strain O52YYT having deposit accession number DSM 32561 or a strain having all the identifying characteristics of *Bacillus amyloliquefaciens* strain DSM 32561 or a mutant thereof.

In another aspect, the invention relates to a composition comprising a carrier and one or more of the bacteria cultures having characteristics substantially identical to that of *Bacillus pumilus* strain O72NR7 having deposit accession number DSM 32563 or a strain having all the identifying characteristics of *Bacillus pumilus* strain DSM 32563 or a mutant thereof.

In an embodiment, the composition further comprises one or more additional microbes. In a particular embodiment, the composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a particular embodiment, the composition further comprises a bacterium from one or more of the following strains of *Bacillus amyloliquefaciens, Bacillus subtilis, Bacillus*

*pumilus, Bacillus polymyxa, Bacillus licheniformis, Bacillus megaterium, Bacillus coagulans, Bacillus circulans*, or any combination thereof.

In a particular embodiment, the composition further comprises one or more types of yeast. The one or more types of yeast can be selected from the group consisting of *Saccharomycetaceae, Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and *Basidiomycota*.

In an embodiment to any of the aforementioned embodiments the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose, farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000 and carbopol.

In another embodiment, the composition described herein can optionally include one or more enzymes. Enzymes can be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, The ENZYME database, 2000, *Nucleic Acids Res.* 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at URL: http://afmb.cnrs-mrs.fr/~cazy/CAZY/index-.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23).

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX and G2 (DSM Nutritional Products), Econase® XT and Barley (AB Vista), Xylathin® (Verenium), Axtra® XB (Xylanase/beta-glucanase, DuPont), Rovabio® excel (Adisseo), and Rovabio Advance® (Adisseo).

In a particular embodiment, the composition of the invention comprises a protease (EC 3.4). Examples of commercially available proteases include Ronozyme® ProAct (DSM Nutritional Products).

The composition of the invention can, e.g., be manufactured as mash composition (non-pelleted) or pelleted composition. The bacteria cultures, such a e.g. *Bacillus* strains, and optionally enzymes can be added as solid or liquid formulations. For example, for mash composition a solid or liquid culture formulation may be added before or during the ingredient mixing step. Typically, a liquid culture preparation comprises the culture of the invention optionally with a polyol, such as glycerol, ethylene glycol or propylene glycol, and is added after the pelleting step, such as by spraying the liquid formulation onto the pellets.

The enzyme may be added to the composition as a granule, which is optionally pelleted or extruded. The granule typically comprises a core particle and one or more coatings, which typically are salt and/or wax coatings. The core particle can either be a homogeneous blend of an active compound optionally together with salts (e.g., organic or inorganic zinc or calcium salt) or an inert particle with an active compound applied onto it. The active compound is the culture of the invention optionally combined with one or more enzymes. The inert particle may be water soluble or water insoluble, e.g., starch, a sugar (such as sucrose or lactose), or a salt (such as NaCl, $Na_2SO_4$) The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

The present invention also relates to animal feed additives comprising one or more *Bacillus* strains. Thus, in one embodiment, the invention relates to an animal feed additive comprising a *Bacillus* strain, wherein:
 i) the *Bacillus* strain has activity against an *Lawsonia intracellularis* infection, and
 ii) the *Bacillus* strain improves body weight gain (BWG) and/or average daily gain (ADG) and/or feed conversion ratio (FCR) in animals fed with the *Bacillus* strain.

In another aspect, the invention relates to animal feed additives comprising one or more *Bacillus* strains, which is selected from the group consisting of:
 a. *Bacillus licheniformis* strain O42AH3 having deposit accession number DSM 32559 or a strain having all the identifying characteristics of *Bacillus licheniformis* strain DSM 32559 or a mutant thereof,
b. *Bacillus subtilis* strain O52YJ6 having deposit accession number DSM 32560 or a strain having all the identifying characteristics of *Bacillus subtilis* strain DSM 32560 or a mutant thereof,
c. *Bacillus amyloliquefaciens* strain O52YYT having deposit accession number DSM 32561 or a strain having all the identifying characteristics of *Bacillus amyloliquefaciens* strain DSM 32561 or a mutant thereof,
d. *Bacillus pumilus* strain O72NR7 having deposit accession number DSM 32563 or a strain having all the identifying characteristics of *Bacillus pumilus* strain DSM 32563 or a mutant thereof, and
e. *Bacillus subtilis* strain SB3175 having deposit accession number NRRL B-50605 or a strain having all the identifying characteristics of *Bacillus subtilis* strain NRRL B-50605 or a mutant thereof.

In another aspect, the invention relates to animal feed additives comprising one or more *Bacillus* strains, which is selected from the group consisting of:
a. *Bacillus licheniformis* strain O42AH3 having deposit accession number DSM 32559 or a strain having all the identifying characteristics of *Bacillus licheniformis* strain DSM 32559 or a mutant thereof,
b. *Bacillus subtilis* strain O52YJ6 having deposit accession number DSM 32560 or a strain having all the identifying characteristics of *Bacillus subtilis* strain DSM 32560 or a mutant thereof,
c. *Bacillus amyloliquefaciens* strain O52YYT having deposit accession number DSM 32561 or a strain having all the identifying characteristics of *Bacillus amyloliquefaciens* strain DSM 32561 or a mutant thereof, and
d. *Bacillus pumilus* strain O72NR7 having deposit accession number DSM 32563 or a strain having all the identifying characteristics of *Bacillus subtilis* strain DSM 32563 or a mutant thereof.

In another aspect, the invention relates to animal feed additives comprising one or more *Bacillus* strains, which is selected from the group consisting of:
a. *Bacillus amyloliquefaciens* strain O52YYT having deposit accession number DSM 32561 or a strain having all the identifying characteristics of *Bacillus amyloliquefaciens* strain DSM 32561 or a mutant thereof, and
b. *Bacillus pumilus* strain O72NR7 having deposit accession number DSM 32563 or a strain having all the identifying characteristics of *Bacillus pumilus* strain DSM 32563 or a mutant thereof.

In another aspect, the invention relates to animal feed additives comprising *Bacillus amyloliquefaciens* strain O52YYT having deposit accession number DSM 32561 or a strain having all the identifying characteristics of *Bacillus amyloliquefaciens* strain DSM 32561 or a mutant thereof.

In another aspect, the invention relates to animal feed additives comprising *Bacillus pumilus* strain O72NR7 having deposit accession number DSM 32563 or a strain having all the identifying characteristics of *Bacillus pumilus* strain DSM 32563 or a mutant thereof.

In an embodiment, the amount of *Bacillus* strain in the animal feed additive is between 0.001% and 10% by weight of the composition.

In an embodiment, the animal feed additive comprises one or more formulating agents, preferably as described herein above.

In an embodiment, the animal feed additive comprises one or more further enzymes, preferably as described herein below.

In an embodiment, the animal feed additive comprises one or more additional probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

The present invention also relates to animal feed compositions comprising *Bacillus* strains of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Swine diets can be characterized as indicated in Table B of WO 01/58275, columns 2-3.

An animal feed composition according to the invention has a crude protein content of 50-800 g/kg, and furthermore comprises at least one *Bacillus* strain as claimed herein.

Furthermore, or in the alternative (to the crude protein content indicated above), the animal feed composition of the invention has a content of metabolizable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolizable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolizable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. *Bacillus* strains can be added as solid or liquid *Bacillus* formulations. For example, for mash feed a solid or liquid *Bacillus* formulation may be added before or during the ingredient mixing step. For pelleted feed the (liquid or solid) *Bacillus* preparation may also be added before or during the feed ingredient step. Typically, a liquid *Bacillus* preparation comprises the *Bacillus* strain of the invention optionally with a polyol, such as glycerol, ethylene glycol or propylene glycol, and is added after the pelleting step, such as by spraying the liquid formulation onto the pellets. The *Bacillus* strain may also be incorporated in a feed additive or premix.

Alternatively, the *Bacillus* strain can be prepared by freezing a mixture of *Bacillus* solution with a bulking agent such as ground soybean meal, and then lyophilizing the mixture.

The final *Bacillus* strain concentration in the diet is within the range of 0.01-200 mg *Bacillus* strain per kg diet, preferably between 0.05-100 mg/kg diet, more preferably 0.1-50 mg, even more preferably 0.2-20 mg *Bacillus* strain per kg animal diet.

It is at present contemplated that the *Bacillus* strain is administered in one or more of the following amounts (dosage ranges): 0.01-200; 0.05-100; 0.1-50; 0.2-20; 0.1-1; 0.2-2; 0.5-5; or 1-10;—all these ranges being in mg *Bacillus* strains per kg feed (ppm).

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

Thus, in a further aspect, the present invention also relates to an animal feed comprising one or more *Bacillus* strains and plant based material. In another aspect, the present invention also relates to an animal feed comprising the animal feed additive of the invention (as described herein above) and plant based material.

In one embodiment, the invention relates to an animal feed comprising plant based material and one or more *Bacillus* strains such as two or more up to and including all of the strains in the group consisting of:

a. *Bacillus licheniformis* strain O42AH3 having deposit accession number DSM 32559 or a strain having all the identifying characteristics of *Bacillus licheniformis* strain DSM 32559 or a mutant thereof, b. *Bacillus subtilis* strain O52YJ6 having deposit accession number DSM 32560 or a strain having all the identifying characteristics of *Bacillus subtilis* strain DSM 32560 or a mutant thereof, c. *Bacillus amyloliquefaciens* strain O52YYT having deposit accession number DSM 32561 or a strain having all the identifying characteristics of *Bacillus amyloliquefaciens* strain DSM 32561 or a mutant thereof, d. *Bacillus pumilus* strain O72NR7 having deposit accession number DSM 32563 or a strain having all the identifying characteristics of *Bacillus pumilus* strain DSM 32563 or a mutant thereof, and e. *Bacillus subtilis* strain SB3175 having deposit accession number NRRL B-50605 or a strain having all the identifying characteristics of *Bacillus subtilis* strain NRRL B-50605 or a mutant thereof.

In one embodiment, the invention relates to an animal feed comprising plant based material and one or more *Bacillus* strains such as two or more up to and including all of the strains in the group consisting of:

a. *Bacillus licheniformis* strain O42AH3 having deposit accession number DSM 32559 or a strain having all the identifying characteristics of *Bacillus licheniformis* strain DSM 32559 or a mutant thereof, b. *Bacillus subtilis* strain O52YJ6 having deposit accession number DSM 32560 or a strain having all the identifying characteristics of *Bacillus subtilis* strain DSM 32560 or a mutant thereof, c. *Bacillus amyloliquefaciens* strain O52YYT having deposit accession number DSM 32561 or a strain having all the identifying characteristics of *Bacillus amyloliquefaciens* strain DSM 32561 or a mutant thereof, and d. *Bacillus pumilus* strain O72NR7 having deposit accession number DSM 32563 or a strain having all the identifying characteristics of *Bacillus pumilus* strain DSM 32563 or a mutant thereof.

In one embodiment, the invention relates to an animal feed comprising plant based material and one or more *Bacillus* strains, such as two *Bacillus* strains, selected from the group consisting of:

a. *Bacillus amyloliquefaciens* strain O52YYT having deposit accession number DSM 32561 or a strain having all the identifying characteristics of *Bacillus amyloliquefaciens* strain DSM 32561 or a mutant thereof, and b. *Bacillus pumilus* strain O72NR7 having deposit accession number DSM 32563 or a strain having all the identifying characteristics of *Bacillus pumilus* strain DSM 32563 or a mutant thereof.

In one embodiment, the invention relates to an animal feed comprising plant based material and *Bacillus amyloliquefaciens* strain O52YYT having deposit accession number DSM 32561 or a strain having all the identifying characteristics of *Bacillus amyloliquefaciens* strain DSM 32561 or a mutant thereof.

In one embodiment, the invention relates to an animal feed comprising plant based material and *Bacillus pumilus* strain O72NR7 having deposit accession number DSM 32563 or a strain having all the identifying characteristics of *Bacillus pumilus* strain DSM 32563 or a mutant thereof.

In a preferred embodiment, the animal feed comprises one or more bacterial strains described herein, wherein the bacterial count of each of the bacterial strains is between $1 \times 10^4$ and $1 \times 10^{12}$ CFU/kg of animal feed, preferably between $1 \times 10^7$ and $1 \times 10^{11}$ CFU/kg of animal feed, more preferably between $1 \times 10^8$ and $1 \times 10^{10}$ CFU/kg of animal feed and most preferably between $1 \times 10^8$ and $1 \times 10^9$ CFU/kg of animal feed.

In a preferred embodiment, the bacterial count of each of the bacterial strains in the animal feed is between $1 \times 10^4$ and $1 \times 10^{12}$ CFU/kg of dry matter, preferably between $1 \times 10^6$ and $1 \times 10^{11}$ CFU/kg of dry matter, more preferably between $1 \times 10^8$ and $1 \times 10^{10}$ CFU/kg of dry matter and most preferably between $1 \times 10^8$ and $1 \times 10^9$ CFU/kg of dry matter.

In a preferred embodiment, the animal feed has a bacterial count of each *Bacillus* spore between $1 \times 10^3$ and $1 \times 10^{13}$ CFU/animal/day, preferably between $1 \times 10^5$ and $1 \times 10^{11}$ CFU/animal/day, more preferably between $1 \times 10^6$ and $1 \times 10^{10}$ CFU/animal/day and most preferably between $1 \times 10^7$ and $1 \times 10^9$ CFU/animal/day.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

In a further embodiment, the animal feed has been pelleted.

Preferred embodiments of the invention are described in the set of items herein below 1. One or more *Bacillus* strains characterized in that:
   i) the *Bacillus* strain has activity against *Lawsonia intracellularis* infection, and
   ii) the *Bacillus* strain improves body weight gain (BWG) and/or average daily gain (ADG) and/or Feed Conversion Ratio (FCR) in animals fed with the *Bacillus* strain.

2. One or more *Bacillus* strains having activity against *Lawsonia intracellularis* infection, wherein the strains reduce the number of heavily infected cells (HIC) in a method comprising the steps:
   i) preparing a filtered cell-free extract comprising the *Bacillus* strain(s), Tryptic soy broth with yeast extract (TSBYE) and heat killed *E. coli*;
   ii) from the extract of step i) preparing *Bacillus* supernatant dilutions comprising *Lawsonia intracellularis*;
   iii) incubating the dilutions of step ii);
   iv) adding the incubated dilutions of step iii) to murine fibroblast McCoy host cells;
   v) incubating the host cells of step iv) to allow for *Lawsonia intracellularis* to infect the McCoy host cells;
   vi) counting the number of heavily infected cells (HIC); and
   vii) comparing the count from step vi) to the count of HIC in control cells prepared according to steps i) to v) but not comprising the *Bacillus* strains;
   wherein the number of HIC is reduced at least 30% compared to the control cells.

3. The *Bacillus* strain according to item 1 or 2, wherein the *Bacillus* strain reduces the effect of inflammation on Electrical Resistance in Caco-2 cells in vitro compared to the effect of inflammation on Electrical Resistance in Caco-2 cells in vitro without the *Bacillus* strain, wherein the effect of inflammation on Electrical Resistance is measured in a trans-epithelial electrical resistance (TEER) test.

4. The *Bacillus* strain according to any one of items 1 to 3, wherein the *Bacillus* strain decreases the relative abundance of one or more members of the phylum Proteobacteria in the intestinal microbiome of animals fed with feed comprising the *Bacillus* strain compared to animals fed with the same feed without the *Bacillus* strain.

5. The *Bacillus* strain according to item 4 wherein the one or more members of the phylum Proteobacteria is selected from the group consisting of: *Escherichia*, *Shigella*, *Campylobacter*, *Burkholderia*, *Acinetobacter* and any combination thereof.

6. The *Bacillus* strain according to any one of the preceding items, wherein the *Bacillus* strain increases the relative abundance of one or more members of a specific genera selected from the group consisting of: *Ruminococcus*, *Blautia*, *Lactobacillus*, *Faecalibacterium*, and *Megasphera* in the intestinal microbiome of animals fed with feed comprising the *Bacillus* strain compared to animals fed with the same feed without the *Bacillus* strain.

7. The *Bacillus* strain according to any one of the preceding items, wherein lesions in the intestinal tract of an animal are reduced after feeding the *Bacillus* strain to the animal for at least 24 hours, such as at least 36 hours, 2 days, 3 days, 4 days, 5 days, 6 days or 1 week, where the lesions are reduced compared to lesions in the intestinal tract of an animal not fed with *Bacillus* strains.

8. The *Bacillus* strain according to any one of the preceding items, wherein lesions in the intestinal tract of an animal are reduced after feeding the *Bacillus* strain to the animal for at least 2 weeks, such as at least 3 weeks, 4 weeks, 1 month, 2 months, 3 months, 4 months, 5 months, 6 months or 1 year, where the lesions are reduced compared to lesions in the intestinal tract of an animal not fed with *Bacillus* strains.

9. The *Bacillus* strain according to any one of the preceding items, wherein the *Bacillus* strain is selected from *Bacillus pumilus* O72NR7 having deposit accession number DSM 32563, *Bacillus licheniformis* O42AH3 having deposit accession number DSM 32559 and any combination thereof.

10. The *Bacillus* strain according to any one of the preceding items, wherein the *Bacillus* strain comprises 16S rDNA that is more than 98% sequence identity to SEQ ID NO: 1 and/or more than 98% sequence identity to SEQ ID NO: 2 and/or more than 98% sequence identity to SEQ ID NO: 3 and/or more than 98% sequence identity to SEQ ID NO: 4 and/or more than 98% sequence identity to SEQ ID NO: 11 and/or more than 98% sequence identity to SEQ ID NO: 12.

11. The *Bacillus* strains according to any one of the preceding items to the extent possible, wherein the *Bacillus* strain(s) is one or more *Bacillus subtilis* strains, one or more *Bacillus licheniformis* strains, one or more *Bacillus pumilus* strains or one or more *Bacillus amyloliquefaciens* strains, and any combination thereof.

12. The *Bacillus* strains according to any one of the preceding items to the extent possible, wherein the *Bacillus* strain(s) is one or more *Bacillus subtilis* strains, one or more *Bacillus licheniformis* strains and/or one or more *Bacillus pumilus* strains.

13. The *Bacillus* strains according to any one of the preceding items, wherein the *Bacillus* strain is one or more *Bacillus subtilis* strains.

14. The *Bacillus* strains according to any one of the preceding items, wherein the *Bacillus* strain is one or more *Bacillus licheniformis* strains.

15. The *Bacillus* strains according to any one of the preceding items, wherein the *Bacillus* strain is one or more *Bacillus pumilus* strains.

16. The *Bacillus* strains according to any one of the preceding items, wherein the *Bacillus* strain is selected from the group consisting of:
   *Bacillus licheniformis* strain O42AH3 having deposit accession number DSM 32559 or a strain having all the identifying characteristics of *Bacillus licheniformis* strain DSM 32559 or a mutant thereof,
   *Bacillus subtilis* strain O52YJ6 having deposit accession number DSM 32560 or a strain having all the identifying characteristics of *Bacillus subtilis* strain DSM 32560 or a mutant thereof,
   *Bacillus amyloliquefaciens* strain O52YYT having deposit accession number DSM 32561 or a strain having all the identifying characteristics of *Bacillus amyloliquefaciens* strain DSM 32561 or a mutant thereof,
   *Bacillus pumilus* strain O72NR7 having deposit accession number DSM 32563 or a strain having all the identifying characteristics of *Bacillus pumilus* strain DSM 32563 or a mutant thereof, and
   *Bacillus subtilis* strain SB3175 having deposit accession number NRRL B-50605 or a strain having all the identifying characteristics of *Bacillus subtilis* strain NRRL B-50605 or a mutant thereof.

17. The *Bacillus* strains according to any one of the preceding items, wherein the *Bacillus* strain is selected from the group consisting of:
   *Bacillus amyloliquefaciens* strain O52YYT having deposit accession number DSM 32561 or a strain having all the identifying characteristics of *Bacillus amyloliquefaciens* strain DSM 32561 or a mutant thereof, and
   *Bacillus pumilus* strain O72NR7 having deposit accession number DSM 32563 or a strain having all the identifying characteristics of *Bacillus pumilus* strain DSM 32563 or a mutant thereof.

18. One or more isolated *Bacillus* strains selected from the group consisting of:
   *Bacillus licheniformis* strain O42AH3 having deposit accession number DSM 32559 or a strain having all the identifying characteristics of *Bacillus licheniformis* strain DSM 32559 or a mutant thereof,
   *Bacillus subtilis* strain O52YJ6 having deposit accession number DSM 32560 or a strain having all the identifying characteristics of *Bacillus subtilis* strain DSM 32560 or a mutant thereof,
   *Bacillus amyloliquefaciens* strain O52YYT having deposit accession number DSM 32561 or a strain having all the identifying characteristics of *Bacillus amyloliquefaciens* strain DSM 32561 or a mutant thereof, and
   *Bacillus pumilus* strain O72NR7 having deposit accession number DSM 32563 or a strain having all the identifying characteristics of *Bacillus pumilus* strain DSM 32563 or a mutant thereof, and
   *Bacillus subtilis* strain SB3175 having deposit accession number NRRL B-50605 or a strain having all the identifying characteristics of *Bacillus subtilis* strain NRRL B-50605 or a mutant thereof.

19. One or more isolated *Bacillus* strains selected from the group consisting of:
   *Bacillus amyloliquefaciens* strain O52YYT having deposit accession number DSM 32561 or a strain having all the identifying characteristics of *Bacillus amyloliquefaciens* strain DSM 32561 or a mutant thereof, and
   *Bacillus pumilus* strain O72NR7 having deposit accession number DSM 32563 or a strain having all the identifying characteristics of *Bacillus pumilus* strain DSM 32563 or a mutant thereof.

20. The *Bacillus* strains according to any one of the preceding items, wherein the *Bacillus* strain is non-hemolytic.

21. The *Bacillus* strains according to any one of the preceding items, wherein the *Bacillus* strain has activity against *Lawsonia intracellularis* as determined in Example 4.

22. The *Bacillus* strains according to any one of the preceding items, wherein *Lawsonia intracellularis* is prevented or alleviated in production animals.

23. The *Bacillus* strains according to any one of the preceding items, wherein the production animals are selected from the group consisting of: Horses, guinea pigs, swine, pigs, piglets, growing pigs, sows, boars, hamsters, and monogastric animals.

24. The *Bacillus* strains according to any one of the preceding items, wherein the production animals are selected from the group consisting of: pigs, swine, piglets, growing pigs, and sows.

25. The *Bacillus* strains according to any one of the preceding items, wherein the *Bacillus* strain is the *Bacillus licheniformis* strain O42AH3 having deposit accession number DSM 32559 or a strain having all the identifying characteristics of *Bacillus licheniformis* strain DSM 32559 or a mutant thereof.

26. The *Bacillus* strains according to any one of the preceding items, wherein the *Bacillus* strain is the *Bacillus subtilis* strain O52YJ6 having deposit accession number DSM 32560 or a strain having all the identifying characteristics of *Bacillus subtilis* strain DSM 32560 or a mutant thereof.

27. The *Bacillus* strains according to any one of the preceding items, wherein the *Bacillus* strain is the *Bacillus amyloliquefaciens* strain O52YYT having deposit accession number DSM 32561 or a strain having all the identifying characteristics of *Bacillus amyloliquefaciens* strain DSM 32561 or a mutant thereof.

28. The *Bacillus* strains according to any one of the preceding items, wherein the *Bacillus* strain is the *Bacillus*

*pumilus* strain O72NR7 having deposit accession number DSM 32563 or a strain having all the identifying characteristics of *Bacillus pumilus* strain DSM 32563 or a mutant thereof.

29. The *Bacillus* strains according to any one of the preceding items, wherein the *Bacillus* spores of the *Bacillus* strains are present as dried spores.

30. The *Bacillus* strains according to any one of the preceding items, wherein at least 70% (such as at least 80% or at least 90%) of the *Bacillus* spores survive the gastric environment in a swine such as e.g. pigs, piglets, growing pigs, or sows.

31. The *Bacillus* strains according to any one of the preceding items which are derived from a substantially pure culture.

32. A *Bacillus* strain which is the *Bacillus licheniformis* strain O42AH3 having deposit accession number DSM 32559 or a strain having all the identifying characteristics of *Bacillus licheniformis* strain DSM 32559 or a mutant thereof.

33. A *Bacillus* strain which is the *Bacillus subtilis* strain O52YJ6 having deposit accession number DSM 32560 or a strain having all the identifying characteristics of *Bacillus subtilis* strain DSM 32560 or a mutant thereof.

34. A *Bacillus* strain which is the *Bacillus amyloliquefaciens* strain O52YYT having deposit accession number DSM 32561 or a strain having all the identifying characteristics of *Bacillus amyloliquefaciens* strain DSM 32561 or a mutant thereof.

35. A *Bacillus* strain which is the *Bacillus pumilus* strain O72NR7 having deposit accession number DSM 32563 or a strain having all the identifying characteristics of *Bacillus pumilus* strain DSM 32563 or a mutant thereof.

36. A composition comprising one or more *Bacillus* strains, wherein the *Bacillus* strain is characterized in that:
   i) the *Bacillus* strain has activity against *Lawsonia intracellularis* infection, and
   ii) the *Bacillus* strain improves body weight gain (BWG) and/or average daily gain (ADG) and/or Feed Conversion Ratio (FCR) in animals fed with the *Bacillus* strain.

37. A composition comprising one or more *Bacillus* strains having activity against *Lawsonia intracellularis* infection, wherein the strains of the composition reduce the number of heavily infected cells (HIC) in a method comprising the steps:
   i) preparing a filtered cell-free extract comprising the *Bacillus* strain(s), Tryptic soy broth with yeast extract (TSBYE) and heat killed *E. coli*;
   ii) from the extract of step i) preparing *Bacillus* supernatant dilutions comprising *Lawsonia intracellularis*;
   iii) incubating the dilutions of step ii);
   iv) adding the incubated dilutions of step iii) to murine fibroblast McCoy host cells;
   v) incubating the host cells of step iv) to allow for *Lawsonia intracellularis* to infect the McCoy host cells;
   vi) counting the number of heavily infected cells (HIC); and
   vii) comparing the count from step vi) to the count of HIC in control cells prepared according to steps i) to v) but not comprising the *Bacillus* strains;
   wherein the number of HIC is reduced at least 30% compared to the control cells.

38. The composition according to item 36 or 37, wherein the *Bacillus* strain of the composition reduces the effect of inflammation on Electrical Resistance in Caco-2 cells in vitro compared to the effect of inflammation on Electrical Resistance in Caco-2 cells in vitro without the *Bacillus* strain,
   wherein the effect of inflammation on Electrical Resistance is measured in a trans-epithelial electrical resistance (TEER) test.

39. The composition according to any one of items 36 to 38, wherein the *Bacillus* strain of the composition decreases the relative abundance of one or more members of the phylum Proteobacteria in the intestinal microbiome of animals fed with a composition comprising the *Bacillus* strain compared to animals fed with the same composition without the *Bacillus* strain.

40. The composition according to item 39, wherein the one or more members of the phylum Proteobacteria is selected from the group consisting of: *Escherichia, Shigella, Campylobacter, Burkholderia, Acinetobacter* and any combination thereof.

41. The composition according to any one of items 36 to 40, wherein the *Bacillus* strain of the composition increases the relative abundance of one or more members of a specific genera selected from the group consisting of: *Ruminococcus, Blautia, Lactobacillus, Faecalibacterium*, and *Megasphera* in the intestinal microbiome of animals fed with a composition comprising the *Bacillus* strain compared to animals fed with the same a composition without the *Bacillus* strain.

42. The composition according to any one of items 36 to 41, wherein lesions in the intestinal tract of an animal are reduced after feeding the composition to the animal for at least 24 hours, such as at least 36 hours, 2 days, 3 days, 4 days, 5 days, 6 days or 1 week, where the lesions are reduced compared to lesions in the intestinal tract of an animal not fed with a composition comprising a *Bacillus* strain.

43. The composition according to any one of items 36 to 42, wherein lesions in the intestinal tract of an animal are reduced after feeding the composition to the animal for at least 2 weeks, such as at least 3 weeks, 4 weeks, 1 month, 2 months, 3 months, 4 months, 5 months, 6 months or 1 year, where the lesions are reduced compared to lesions in the intestinal tract of an animal not fed with a composition comprising a *Bacillus* strain.

44. The composition according to any one of items 36 to 43, wherein the one or more *Bacillus* strains is selected from the group consisting of:
   *Bacillus licheniformis* strain O42AH3 having deposit accession number DSM 32559 or a strain having all the identifying characteristics of *Bacillus licheniformis* strain DSM 32559 or a mutant thereof,
   *Bacillus subtilis* strain O52YJ6 having deposit accession number DSM 32560 or a strain having all the identifying characteristics of *Bacillus subtilis* strain DSM 32560 or a mutant thereof,
   *Bacillus amyloliquefaciens* strain O52YYT having deposit accession number DSM 32561 or a strain having all the identifying characteristics of *Bacillus amyloliquefaciens* strain DSM 32561 or a mutant thereof,
   *Bacillus pumilus* strain O72NR7 having deposit accession number DSM 32563 or a strain having all the identifying characteristics of *Bacillus pumilus* strain DSM 32563 or a mutant thereof, and
   *Bacillus subtilis* strain SB3175 having deposit accession number NRRL B-50605 or a strain having all the identifying characteristics of *Bacillus subtilis* strain NRRL B-50605 or a mutant thereof.

45. A composition comprising one or more *Bacillus* strains selected from the group consisting of:
- *Bacillus licheniformis* strain O42AH3 having deposit accession number DSM 32559 or a strain having all the identifying characteristics of *Bacillus licheniformis* strain DSM 32559 or a mutant thereof,
- *Bacillus subtilis* strain O52YJ6 having deposit accession number DSM 32560 or a strain having all the identifying characteristics of *Bacillus subtilis* strain DSM 32560 or a mutant thereof,
- *Bacillus amyloliquefaciens* strain O52YYT having deposit accession number DSM 32561 or a strain having all the identifying characteristics of *Bacillus amyloliquefaciens* strain DSM 32561 or a mutant thereof,
- *Bacillus pumilus* strain O72NR7 having deposit accession number DSM 32563 or a strain having all the identifying characteristics of *Bacillus pumilus* strain DSM 32563 or a mutant thereof, and
- *Bacillus subtilis* strain SB3175 having deposit accession number NRRL B-50605 or a strain having all the identifying characteristics of *Bacillus subtilis* strain NRRL B-50605 or a mutant thereof.

46. The composition according to any one of items 36 to 45, wherein the one or more *Bacillus* strains are in spore form.

47. The composition according to any one of items 36 to 46, which further comprises calcium carbonate.

48. The composition according to any one of items 36 to 47, wherein the *Bacillus* strains are derived from a substantially pure culture.

49. Use of one or more *Bacillus* strains for prevention and/or alleviation of *Lawsonia intracellularis* in an animal.

50. The use of one or more *Bacillus* strains according to item 49, wherein the *Bacillus* strains have activity against *Lawsonia intracellularis* infection and reduce the number of heavily infected cells (HIC) in a method comprising the steps:
- i) preparing a filtered cell-free extract comprising the *Bacillus* strain(s), Tryptic soy broth with yeast extract (TSBYE) and heat killed *E. coli*;
- ii) from the extract of step i) preparing *Bacillus* supernatant dilutions comprising *Lawsonia intracellularis*;
- iii) incubating the dilutions of step ii);
- iv) adding the incubated dilutions of step iii) to murine fibroblast McCoy host cells;
- v) incubating the host cells of step iv) to allow for *Lawsonia intracellularis* to infect the McCoy host cells;
- vi) counting the number of heavily infected cells (HIC); and
- vii) comparing the count from step vi) to the count of HIC in control cells prepared according to steps i) to v) but not comprising the *Bacillus* strains;
wherein the number of HIC is reduced at least 30% compared to the control cells.

51. The use of one or more *Bacillus* strains according to item 49 or 50, wherein
- i) the *Bacillus* strain has activity against *Lawsonia intracellularis*, and
- ii) the *Bacillus* strain improves body weight gain (BWG) and/or average daily gain (ADG) and/or feed conversion ratio (FCR) in animals fed with the *Bacillus* strain.

52. The use of one or more *Bacillus* strains according to any one of items 49 to 51, wherein the *Bacillus* strain reduces the effect of inflammation on Electrical Resistance in Caco-2 cells in vitro compared to the effect of inflammation on Electrical Resistance in Caco-2 cells in vitro without the *Bacillus* strain,
wherein the effect of inflammation on Electrical Resistance is measured in a trans-epithelial electrical resistance (TEER) test.

53. The use of one or more *Bacillus* strains according to any one of items 49 to 52, wherein the *Bacillus* strain decreases the relative abundance of one or more members of the phylum Proteobacteria in the intestinal microbiome of animals fed with feed comprising the *Bacillus* strain compared to animals fed with the same feed without the *Bacillus* strain.

54. The use of one or more *Bacillus* strains according to item 53, wherein the one or more members of the phylum Proteobacteria is selected from the group consisting of: *Escherichia, Shigella, Campylobacter, Burkholderia, Acinetobacter* and any combination thereof.

55. The use of one or more *Bacillus* strains according to any one of items 49 to 54, wherein the *Bacillus* strain increases the relative abundance of one or more members of a specific genera selected from the group consisting of: *Ruminococcus, Blautia, Lactobacillus, Faecalibacterium,* and *Megasphera* in the intestinal microbiome of animals fed with feed comprising the *Bacillus* strain compared to animals fed with the same feed without the *Bacillus* strain.

56. The use of one or more *Bacillus* strains according to any one of items 49 to 55, wherein lesions in the intestinal tract of an animal are reduced after feeding the *Bacillus* strain to the animal for at least 24 hours, such as at least 36 hours, 2 days, 3 days, 4 days, 5 days, 6 days or 1 week, where the lesions are reduced compared to lesions in the intestinal tract of an animal not fed with *Bacillus* strains.

57. The use of one or more *Bacillus* strains according to any one of items 49 to 56, wherein lesions in the intestinal tract of an animal are reduced after feeding the *Bacillus* strain to the animal for at least 2 weeks, such as at least 3 weeks, 4 weeks, 1 month, 2 months, 3 months, 4 months, 5 months, 6 months or 1 year, where the lesions are reduced compared to lesions in the intestinal tract of an animal not fed with *Bacillus* strains.

58. The use of one or more *Bacillus* strains according to any one of items 49 to 57, wherein the one or more *Bacillus* strains is selected from the group consisting of:
- *Bacillus licheniformis* strain O42AH3 having deposit accession number DSM 32559 or a strain having all the identifying characteristics of *Bacillus licheniformis* strain DSM 32559 or a mutant thereof,
- *Bacillus subtilis* strain O52YJ6 having deposit accession number DSM 32560 or a strain having all the identifying characteristics of *Bacillus subtilis* strain DSM 32560 or a mutant thereof,
- *Bacillus amyloliquefaciens* strain O52YYT having deposit accession number DSM 32561 or a strain having all the identifying characteristics of *Bacillus amyloliquefaciens* strain DSM 32561 or a mutant thereof,
- *Bacillus pumilus* strain O72NR7 having deposit accession number DSM 32563 or a strain having all the identifying characteristics of *Bacillus pumilus* strain DSM 32563 or a mutant thereof, and
- *Bacillus subtilis* strain SB3175 having deposit accession number NRRL B-50605 or a strain having all the identifying characteristics of *Bacillus subtilis* strain NRRL B-50605 or a mutant thereof.

59. The use of one or more *Bacillus* strains according to any one of items 49 to 58, wherein the *Bacillus* strain is non-hemolytic.

60. Use of one or more *Bacillus* strains for decreasing the relative abundance of one or more members of the phylum Proteobacteria in the intestinal microbiome of a production animal fed with feed comprising the *Bacillus* strain compared to a production animal fed with the same feed without the *Bacillus* strain and/or increasing the relative abundance of one or more members of a specific genera selected from the group consisting of: *Ruminococcus, Blautia, Lactobacillus, Faecalibacterium,* and *Megasphera* in the intestinal microbiome of a production animal fed with feed comprising the *Bacillus* strain compared to a production animal fed with the same feed without the *Bacillus* strain, wherein the production animal is a ruminant or a non-ruminant such as sheep, goat, cattle, cow, young calve, deer, yank, camel, llama, kangaroo, pig, swine, turkey, duck, chicken, horse, fish or crustacean.

61. An animal feed or feed additive comprising one or more *Bacillus* strains, wherein the *Bacillus* strain is characterized in that:
   i) the *Bacillus* strain has activity against *Lawsonia intracellularis,* and
   ii) the *Bacillus* strain improves body weight gain (BWG) and/or average daily gain (ADG) and/or feed conversion ratio (FCR) in animals fed with the *Bacillus* strain.

62. An animal feed or the animal feed additive comprising one or more *Bacillus* strains having activity against *Lawsonia intracellularis* infection, wherein the strains reduce the number of heavily infected cells (HIC) in a method comprising the steps:
   i) preparing a filtered cell-free extract comprising the *Bacillus* strain(s), Tryptic soy broth with yeast extract (TSBYE) and heat killed *E. coli;*
   ii) from the extract of step i) preparing *Bacillus* supernatant dilutions comprising *Lawsonia intracellularis;*
   iii) incubating the dilutions of step ii);
   iv) adding the incubated dilutions of step iii) to murine fibroblast McCoy host cells;
   v) incubating the host cells of step iv) to allow for *Lawsonia intracellularis* to infect the McCoy host cells;
   vi) counting the number of heavily infected cells (HIC); and
   vii) comparing the count from step vi) to the count of HIC in control cells prepared according to steps i) to v) but not comprising the *Bacillus* strains;
   wherein the number of HIC is reduced at least 30% compared to the control cells.

63. The animal feed or the animal feed additive according to item 61 or 62, wherein the *Bacillus* strain of the composition reduces the effect of inflammation on Electrical Resistance in Caco-2 cells in vitro compared to the effect of inflammation on Electrical Resistance in Caco-2 cells in vitro without the *Bacillus* strain,
   wherein the effect of inflammation on Electrical Resistance is measured in a trans-epithelial electrical resistance (TEER) test.

64. The animal feed or the animal feed additive according to any one of items 61 to 63, wherein the *Bacillus* strain of the animal feed or the animal feed additive decreases the relative abundance of one or more members of the phylum Proteobacteria in the intestinal microbiome of animals fed with feed comprising the *Bacillus* strain compared to animals fed with the same feed without the *Bacillus* strain.

65. The animal feed or the animal feed additive according to item 64, wherein the one or more members of the phylum Proteobacteria is selected from the group consisting of: *Escherichia, Shigella, Campylobacter, Burkholderia, Acinetobacter* and any combination thereof.

66. The animal feed or the animal feed additive according to any one of items 61 to 65, wherein the *Bacillus* strain of the animal feed or the animal feed additive increases the relative abundance of one or more members of a specific genera selected from the group consisting of: *Ruminococcus, Blautia, Lactobacillus, Faecalibacterium,* and *Megasphera* in the intestinal microbiome of animals fed with feed comprising the *Bacillus* strain compared to animals fed with the same feed without the *Bacillus* strain.

67. The animal feed or the animal feed additive according to any one of items 61 to 66, wherein lesions in the intestinal tract of an animal are reduced after feeding the animal feed or the animal feed additive to the animal for at least 24 hours, such as at least 36 hours, 2 days, 3 days, 4 days, 5 days, 6 days or 1 week, where the lesions are reduced compared to lesions in the intestinal tract of an animal not fed with an animal feed or the animal feed additive comprising a *Bacillus* strain.

68. The animal feed or the animal feed additive according to any one of items 61 to 67, wherein lesions in the intestinal tract of an animal are reduced after feeding the animal feed or the animal feed additive to the animal for at least 2 weeks, such as at least 3 weeks, 4 weeks, 1 month, 2 months, 3 months, 4 months, 5 months, 6 months or 1 year, where the lesions are reduced compared to lesions in the intestinal tract of an animal not fed with an animal feed or the animal feed additive comprising a *Bacillus* strain.

69. The animal feed or the animal feed additive according to any one of items 61 to 68, wherein the *Bacillus* strain(s) is one or more *Bacillus subtilis* strains, one or more *Bacillus licheniformis* strains, one or more *Bacillus pumilus* strains and/or one or more *Bacillus amyloliquefaciens* strains.

70. The animal feed or the animal feed additive according to any one of items 61 to 69, wherein the *Bacillus* strain is selected from the group consisting of:
   *Bacillus licheniformis* strain O42AH3 having deposit accession number DSM 32559 or a strain having all the identifying characteristics of *Bacillus licheniformis* strain DSM 32559 or a mutant thereof,
   *Bacillus subtilis* strain O52YJ6 having deposit accession number DSM 32560 or a strain having all the identifying characteristics of *Bacillus subtilis* strain DSM 32560 or a mutant thereof,
   *Bacillus amyloliquefaciens* strain O52YYT having deposit accession number DSM 32561 or a strain having all the identifying characteristics of *Bacillus amyloliquefaciens* strain DSM 32561 or a mutant thereof,
   *Bacillus pumilus* strain O72NR7 having deposit accession number DSM 32563 or a strain having all the identifying characteristics of *Bacillus pumilus* strain DSM 32563 or a mutant thereof, and
   *Bacillus subtilis* strain SB3175 having deposit accession number NRRL B-50605 or a strain having all the identifying characteristics of *Bacillus subtilis* strain NRRL B-50605 or a mutant thereof.

71. An animal feed or feed additive comprising one or more *Bacillus* strains, wherein the *Bacillus* strain is selected from the group consisting of:
   *Bacillus licheniformis* strain O42AH3 having deposit accession number DSM 32559 or a strain having all the identifying characteristics of *Bacillus licheniformis* strain DSM 32559 or a mutant thereof,
   *Bacillus subtilis* strain O52YJ6 having deposit accession number DSM 32560 or a strain having all the identifying characteristics of *Bacillus subtilis* strain DSM 32560 or a mutant thereof,
   *Bacillus amyloliquefaciens* strain O52YYT having deposit accession number DSM 32561 or a strain having all the identifying characteristics of *Bacillus amyloliquefaciens* strain DSM 32561 or a mutant thereof,
   *Bacillus pumilus* strain O72NR7 having deposit accession number DSM 32563 or a strain having all the identifying characteristics of *Bacillus pumilus* strain DSM 32563 or a mutant thereof, and
   *Bacillus subtilis* strain SB3175 having deposit accession number NRRL B-50605 or a strain having all the identifying characteristics of *Bacillus subtilis* strain NRRL B-50605 or a mutant thereof.

72. The animal feed or the animal feed additive according to any one of items 61 to 71, wherein the *Bacillus* strain is non-hemolytic.

73. The animal feed or the animal feed additive according to any one of items 61 to 72, wherein the *Bacillus* strain has activity against *Lawsonia intracellularis* as determined in Example 4.

74. The animal feed or the animal feed additive according to any one of items 61 to 73, wherein the *Bacillus* strain improves one or more performance parameters in an animal selected from the list consisting of body weight gain and/or average daily gain and/or feed conversion rate in an animal fed with the *Bacillus* strain.

75. The animal feed or the animal feed additive according to any one of items 61 to 74, wherein the animal feed or animal feed additive is for animals which are selected from the group consisting of: Horses, guinea pigs, swine, pigs, piglets, growing pigs, sows, boars, hamsters, and monogastric animals.

76. The animal feed or the animal feed additive according to any one of items 61 to 75, wherein the feed or feed additive is for animals which are selected from the group consisting of: pigs, swine, piglets, growing pigs, and sows.

77. The animal feed or the animal feed additive according to any one of items 61 to 76, wherein the *Bacillus* strain is the *Bacillus licheniformis* strain O42AH3 having deposit accession number DSM 32559 or a strain having all the identifying characteristics of *Bacillus licheniformis* strain DSM 32559 or a mutant thereof.

78. The animal feed or the animal feed additive according to any one of items 61 to 77, wherein the *Bacillus* strain is the *Bacillus subtilis* strain O52YJ6 having deposit accession number DSM 32560 or a strain having all the identifying characteristics of *Bacillus subtilis* strain DSM 32560 or a mutant thereof.

79. The animal feed or the animal feed additive according to any one of items 61 to 78, wherein the *Bacillus* strain is the *Bacillus amyloliquefaciens* strain O52YYT having deposit accession number DSM 32561 or a strain having all the identifying characteristics of *Bacillus amyloliquefaciens* strain DSM 32561 or a mutant thereof.

80. The animal feed or the animal feed additive according to any one of items 61 to 79, wherein the *Bacillus* strain is the *Bacillus pumilus* strain O72NR7 having deposit accession number DSM 32563 or a strain having all the identifying characteristics of *Bacillus pumilus* strain DSM 32563 or a mutant thereof.

81. The animal feed or the animal feed additive according to any one of items 61 to 80, wherein the *Bacillus* spores of the animal feed or the animal feed additive are present as dried spores.

82. The animal feed or the animal feed additive according to any one of items 61 to 81, which further comprises a carrier.

83. The animal feed or the animal feed additive according to item 82, wherein the carrier comprises one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

84. The animal feed or the animal feed additive according to any one of items 61 to 83, wherein the animal feed or animal feed additive comprises from $10^5$ to $10^{12}$ CFU/g of isolated *Bacillus* spores.

85. The animal feed or animal feed additive according to any one of items 61 to 84, wherein at least 70% (such as at least 80% or at least 90%) of the *Bacillus* spores survive the gastric environment in a swine such as e.g. pigs, piglets, growing pigs, or sows.

86. The animal feed or animal feed additive according to any one of items 61 to 85 which further comprises one or more components selected from the list consisting of:

one or more enzymes;
one or more additional microbes;
one or more vitamins;
one or more minerals;
one or more amino acids; and
one or more other feed ingredients.

87. The animal feed or animal feed additive according to any one of items 61 to 86, wherein the bacterial count of each *Bacillus* spore is $1\times10^4$ and $1\times10^{14}$ CFU/kg of animal feed or animal feed additive, preferably between $1\times10^6$ and $1\times10^{12}$ CFU/kg of animal feed or animal feed additive, and more preferably between $1\times10^7$ and $1\times10^{11}$ CFU/kg of animal feed or animal feed additive.

88. The animal feed or animal feed additive according to any one of items 61 to 87, wherein the animal feed or animal feed additive is a swine feed or swine feed additive.

89. The animal feed or animal feed additive according to any one of items 61 to 88, wherein the animal feed or animal feed additive is for pigs, swine, piglets, growing pigs, or sows.

90. A method for improving one or more performance parameter(s) in an animal comprising the step of administering one or more *Bacillus* strains according to any of items 1-35 in the feed of the animal.

91. A method of inhibiting *Lawsonia intracellularis* infection in an animal comprising: administering an effective amount of the *Bacillus* strain compositions according to anyone of items 36 to 48 to an animal such as a swine in need thereof.

92. A method of preventing development of severe diarrhea in an animal comprising feeding an effective amount of the *Bacillus* strain composition according to anyone of items 36 to 48 to an animal such as a swine in need thereof for at least 24 hours, such as at least 36 hours, 2 days, 3 days, 4 days, 5 days, 6 days or 1 week.

93. A method of preventing development of severe diarrhea in an animal comprising feeding an effective amount of the *Bacillus* strain composition according to anyone of items 36 to 48 to an animal such as a swine in need thereof for at least 2 weeks, such as at least 3 weeks, 4 weeks, 1 month, 2 months, 3 months, 4 months, 5 months, 6 months or 1 year of feeding the *Bacillus* spore to the animal.

94. A method of decreasing shedding of *Lawsonia intracellularis* in feces of an animal comprising feeding an effective amount of the *Bacillus* strain composition according to anyone of items 36 to 48 to an animal such as a swine in need thereof, where the shedding is decreased compared to shedding of *Lawsonia intracellularis* in feces of animals not fed with *Bacillus* strains.

95. A method according to item 94, wherein the *Bacillus* strain composition is fed to the animal for at least 24 hours, such as at least 36 hours, 2 days, 3 days, 4 days, 5 days, 6 days or 1 week.

96. A method according to item 94, wherein the *Bacillus* strain composition is fed to the animal for at least 2 weeks, such as at least 3 weeks, 4 weeks, 1 month, 2 months, 3 months, 4 months, 5 months, 6 months or 1 year.

97. A method of reducing inflammation in an animal comprising feeding an effective amount of the *Bacillus* strain composition according to anyone of items 36 to 48 to an animal such as a swine in need thereof, wherein the *Bacillus* strain of the composition reduces the effect of inflammation on Electrical Resistance in Caco-2 cells in vitro compared to the effect of inflammation on Electrical Resistance in Caco-2 cells in vitro without the *Bacillus* strain, wherein the effect of inflammation on Electrical Resistance is measured in a trans-epithelial electrical resistance (TEER) test.

98. A method of decreasing the relative abundance of one or more members of the phylum Proteobacteria in the intestinal microbiome of animals comprising feeding an effective amount of the *Bacillus* strain according to anyone of items 36 to 48 to the animal such as a swine in need thereof for at least 24 hours, such as at least 36 hours, 2 days, 3 days, 4 days, 5 days, 6 days or 1 week, where the relative abundance of one or more members of the phylum Proteobacteria is increased compared to the relative abundance of Proteobacteria in animals fed with the same feed for the same period of time without the *Bacillus* strain.

99. A method of decreasing the relative abundance of one or more members of the phylum Proteobacteria in the intestinal microbiome of animals comprising feeding an effective amount of the *Bacillus* strain according to anyone of items 36 to 48 to the animal such as a swine in need thereof for at least 2 weeks, such as at least 3 weeks, 4 weeks, 1 month, 2 months, 3 months, 4 months, 5 months, 6 months or 1 year, where the relative abundance of one or more members of the phylum Proteobacteria is increased compared to the relative abundance of Proteobacteria in animals fed with the same feed for the same period of time without the *Bacillus* strain.

100. The method according to item 98 or 99, wherein the one or more members of the phylum Proteobacteria is selected from the group consisting of: *Escherichia, Shigella, Campylobacter, Burkholderia, Acinetobacter* and any combination thereof.

101. A method of increasing the relative abundance of one or more members of a specific genera selected from the group consisting of: *Ruminococcus, Blautia, Lactobacillus, Faecalibacterium*, and *Megasphera* in the intestinal microbiome of animals comprising feeding an effective amount of the *Bacillus* strain according to anyone of items 36 to 48 to the animal such as a swine in need thereof for at least 24 hours, such as at least 36 hours, 2 days, 3 days, 4 days, 5 days, 6 days or 1 week, where the relative abundance of one or more members of a specific genera selected from the group consisting of: *Ruminococcus, Blautia, Lactobacillus, Faecalibacterium*, and *Megasphera* is increased compared to the relative abundance of the same specific genera in the intestinal microbiome of animals fed with the same feed for the same period of time without the *Bacillus* strain.

102. A method of increasing the relative abundance of one or more members of a specific genera selected from the group consisting of: *Ruminococcus, Blautia, Lactobacillus, Faecalibacterium*, and *Megasphera* in the intestinal microbiome of animals comprising feeding an effective amount of the *Bacillus* strain according to anyone of items 36 to 48 to the animal such as a swine in need thereof for at least 2 weeks, such as at least 3 weeks, 4 weeks, 1 month, 2 months, 3 months, 4 months, 5 months, 6 months or 1 year, where the relative abundance of one or more members of a specific genera selected from the group consisting of: *Ruminococcus, Blautia, Lactobacillus, Faecalibacterium*, and *Megasphera* is increased compared to the relative abundance of the same specific genera in the intestinal microbiome of animals fed with the same feed for the same period of time without the *Bacillus* strain.

103. A method of reducing lesions in the intestinal tract of an animal comprising feeding an effective amount of the *Bacillus* strain composition according to anyone of items 36 to 48 to an animal such as a swine in need thereof for at least 24 hours, such as at least 36 hours, 2 days, 3 days, 4 days, 5 days, 6 days or 1 week, where the lesions are reduced compared to lesions in the intestinal tract of animals not fed with *Bacillus* strains.

104. A method of reducing lesions in the intestinal tract of an animal comprising feeding an effective amount of the *Bacillus* strain composition according to anyone of items 36 to 48 to an animal such as a swine in need thereof for at least 2 weeks, such as at least 3 weeks, 4 weeks, 1 month, 2 months, 3 months, 4 months, 5 months, 6 months or 1 year, where the lesions are reduced compared to lesions in the intestinal tract of an animal not fed with *Bacillus* strains.

105. A method of reducing the IgG score in an animal comprising feeding an effective amount of the *Bacillus* strain composition according to anyone of items 36 to 48 to said animal such as a swine in need thereof for at least 24 hours, such as at least 36 hours, 2 days, 3 days, 4 days, 5 days, 6 days or 1 week, where the IgG score is reduced compared to the IgG score in animals not fed with *Bacillus* strains.

106. A method of reducing the IgG score in an animal comprising feeding an effective amount of the *Bacillus* strain composition according to anyone of items 36 to 48 to said animal such as a swine in need thereof for at least 2 weeks, such as at least 3 weeks, 4 weeks, 1 month, 2 months, 3 months, 4 months, 5 months, 6 months or 1 year, where the IgG score is reduced compared to the IgG score in animals not fed with *Bacillus* strains.

107. A method of increasing the Average Daily Gain of an animal comprising feeding an effective amount of the *Bacillus* strain composition according to anyone of items 36 to 48 to said animal such as a swine in need thereof for at least 24 hours, such as at least 36 hours, 2 days, 3 days, 4 days, 5 days, 6 days or 1 week, where the average Daily gain is increased compared to the Average Daily Gain of animals not fed with *Bacillus* strains.

108. A method of increasing the Average Daily Gain of an animal comprising feeding an effective amount of the *Bacillus* strain composition according to anyone of items 36 to 48 to said animal such as a swine in need thereof for at least 2 weeks, such as at least 3 weeks, 4 weeks, 1 month, 2 months, 3 months, 4 months, 5 months, 6 months or 1 year, where the average Daily gain is increased compared to the Average Daily Gain of animals not fed with *Bacillus* strains.

109. A method of improving the Feed Conversion Rate (FCR) of an animal comprising feeding an effective amount of the *Bacillus* strain composition according to anyone of items 36 to 48 to said animal such as a swine in need thereof for at least 24 hours, such as at least 36 hours, 2 days, 3 days, 4 days, 5 days, 6 days or 1 week, where the FCR is improved compared to the FCR of animals not fed with *Bacillus* strains.

110. A method of improving the Feed Conversion Rate (FCR) of an animal comprising feeding an effective amount of the *Bacillus* strain composition according to anyone of items 36 to 48 to said animal such as a swine in need thereof for at least 2 weeks, such as at least 3 weeks, 4 weeks, 1 month, 2 months, 3 months, 4 months, 5 months, 6 months or 1 year, where the FCR is improved compared to the FCR of animals not fed with *Bacillus* strains.

111. A method of reducing the risk of developing Proliferative Hemorrhagic Enteropathy (PHE) in an animal comprising feeding an effective amount of the *Bacillus* strain composition according to anyone of items 36 to 48 to said animal such as a swine in need thereof for at least 24 hours, such as at least 36 hours, 2 days, 3 days, 4 days, 5 days, 6 days or 1 week, where the risk of developing PHE is improved compared to the same risk in animals not fed with *Bacillus* strains.

112. A method of reducing the risk of developing Proliferative Hemorrhagic Enteropathy (PHE) in an animal comprising feeding an effective amount of the *Bacillus* strain composition according to anyone of items 36 to 48 to said animal such as a swine in need thereof for at least 2 weeks, such as at least 3 weeks, 4 weeks, 1 month, 2 months, 3 months, 4 months, 5 months, 6 months or 1 year, where the risk of developing PHE is improved compared to the same risk in animals not fed with *Bacillus* strains.

EXAMPLES

Example 1—Deposit of Biological Material

*Bacillus licheniformis* strain O42AH3 was deposited on Jul. 11, 2017 under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraße 7 B, 38124 Braunschweig, Germany. The strain was designated deposit accession number DSM 32559 on Jul. 13, 2017. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Bacillus subtilis strain O52YJ6 was deposited on Jul. 11, 2017 under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraße 7 B, 38124 Braunschweig, Germany. The strain was designated deposit accession number DSM 32560 on Jul. 13, 2017. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Bacillus amyloliquefaciens strain O52YYT was deposited on Jul. 11, 2017 under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraße 7 B, 38124 Braunschweig, Germany. The strain was designated deposit accession number DSM 32561 on Jul. 13, 2017. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Bacillus subtilis strain O52YZ6 was deposited on Jul. 11, 2017 under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraße 7 B, 38124 Braunschweig, Germany. The strain was designated deposit accession number DSM 32562 on Jul. 13, 2017. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Bacillus pumilis strain O72NR7 was deposited on Jul. 11, 2017 under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraße 7 B, 38124 Braunschweig, Germany. The strain was designated deposit accession number DSM 32563 on Jul. 13, 2017. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Bacillus subtilis strain SB3175 was deposited on Nov. 30, 2011 under the terms of the Budapest Treaty on the International Recognition of the Deposit of Microorganisms for the Purposes of Patent Procedure at the Agricultural Research Service Culture Collection, 1815 North University Street, Peoria, Illinois 61604, U.S.A. The strain was designated deposit accession number NRRL B-50605. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Sequencing of 16S rDNA Genes

DNA was extracted from a culture of DSM 32559, DSM 32560, DSM 32561 or DSM 32563 using QiaAmp DNA Blood Mini Kit (Qiagen art 51106). The kit was used as recommended for extraction of DNA from gram positive bacteria.

16S rDNA was amplified in a total volume of 50 µl by mixing: 10 pmol of each of Primer 16S F and 16S R, 0.2 mM of each nucleotide, 2.5 units Ampli taq, 1× Ampli taq buffer, 5 µl DNA template and by using the following PCR program: 94° C. 2 min (94° C. 30 s, 52° C. 30 S, 72° C. 1 min)×35, 72° C. 10 min on a Perkin Elmer PCR machine. The PCR product was sequenced by Novozymes DNA sequencing facility using primer 530R, 357F, 1390R and 1100F.

TABLE 1

Primers

| Primer | Sequence | SEQ ID NO |
|---|---|---|
| 16S-F | 5'-GAGTTTGATCCTGGCTCAG-3' | SEQ ID NO: 5 |
| 16S-R | 5'-AGAAAGGAGGTGATCCAGCC-3' | SEQ ID NO: 6 |
| 794-R | 5'-ATCTAATCCTGTTTGCTCCCC-3' | SEQ ID NO: 7 |

TABLE 1-continued

Primers

| Primer | Sequence | SEQ ID NO |
|---|---|---|
| 357-F | 5'-TACGGGAGGCAGCAG-3' | SEQ ID NO: 8 |
| 1390-R | 5'-CGGTGTGTRCAAGGCCC-3' | SEQ ID NO: 9 |
| 1000-F | 5'-CAACGAGCGCAACCCT', | SEQ ID NO: 10 |

Degeneration of primer 1390-R: R is A or G. The 16 S rDNA sequences from DSM 32559, DSM 32560, DSM 32561, DSM 32563, O52YZ5 and O22FHD are shown as SEQ ID NO: 1-4 and 11-12 in the sequence listing respectively. The 16 S rDNA sequences from DSM 32559, DSM 32560, DSM 32561, DSM 32563, O52YZ5 and O22FHD were analyzed by BLAST against EMBL database and showed identity to 16 S rDNA sequences of respectively *Bacillus licheniformis* (SEQ ID NO: 1), *Bacillus subtilis* (SEQ ID NO: 2), *Bacillus amyloliquefaciens* (SEQ ID NO: 3), *Bacillus pumilus* (SEQ ID NO: 4), *Bacillus subtilis* (SEQ ID NO: 11) and *Bacillus subtilis* (SEQ ID NO: 12).

In order to study the phylogenetic affiliation of SEQ ID NO: 1 to SEQ ID NO: 4 and SEQ ID NO: 11 to SEQ ID NO: 12, the sequences were analyzed by a ClustalW alignment in MegAlign (DNASTAR) using SEQ ID NO: 5 to SEQ ID NO: 7 as benchmark. These sequences are reference 16S rDNA sequences of the type strains of *Bacillus vallismortis* taken from AB021198 (SEQ ID NO: 5), *Bacillus subtilis* taken from AJ276351 (SEQ ID NO: 6) and *Bacillus amyloliquefaciens* taken from AB255669 (SEQ ID NO: 7).

The ClustalW alignment of SEQ ID NO: 1 to SEQ ID NO: 7 shows nucleotide positions where 2 or more sequences have a nucleotide that deviates from the other.

Example 2—Cell-Culture Assay Test of Cell-Free Extracts of *Bacillus* for Reduction in Heavy Infected Cells (HIC)

Preparation of TSBYE pH 6.2 Media

Tryptic Soy Broth (30 g/L) was mixed with Yeast Extract (6 g/L) and water pH was adjusted to 6.2 using HCl. The resulting TSBYE media was autoclaved before use.

Preparation of Cell-Free *Bacillus* Extracts

*Bacillus* extracts were prepared over three days. On day 1 of the experiment, sterile culture tubes were prepared with 10 ml of Tryptic soy broth with 0.6% yeast extract (TSBYE) at pH 6.2. The culture tubes were inoculated so that each tube contained a single colony from a plate of a *Bacillus* strain. A separate culture tube was inoculated with a BSL-2 pathogenic isolate of *E. coli* (ATCC10536). Both the *Bacillus* strains and the *E. coli* were incubated overnight at 35° C., with 200 rpm shaking in atmospheric oxygen. On day 2 of the experiment, 1 ml of *E. coli* culture was aliquoted into a microfuge tube. *E. coli* was heat killed in a 80° C. water bath for 30 minutes. After the heat kill, a sample from the microfuge tube was streaked onto SMA plates to ensure all *E. coli* was heat killed. The plate was incubated overnight at 35° C. Sterile culture tubes were prepared with 9 ml of TSBYE pH 6.2 media, 1 ml of heat killed *E. coli* was added to each culture tube, and the tube was inoculated with 100 ul from the *Bacillus* culture prepared on day 1. The cultures were incubated overnight at 35° C. with 200 rpm shaking. On day 3 of the experiment, the primed *Bacillus* overnight cultures were transferred to 15 ml conical tubes. The cells were centrifuged at 8,000 rpm for 10 min and the supernatant was filtered two times through a 0.22 uM filter into a clean, sterile conical tube for use in the in vitro assay for activity against *Lawsonia intracellularis*. A sample of filtered supernatant was streaked onto SMA plates to ensure that all cells had been filtered out. The supernatant was incubated overnight at 35° C. and checked for lack of growth.

Testing of Cell-Free Extracts of *Bacillus* for Activity Against *Lawsonia intracellularis*

*Bacillus* cell-free extracts were evaluated in vitro for activity against *Lawsonia intracellularis* strain GBI06, a recent pathogenic isolate provided by Gut Bugs. Extracts taken from *Bacillus* strains were considered positive if they could reduce the re-infection ability of *Lawsonia intracellularis* by at least 30% following co-incubation. Reduction in *Lawsonia intracellularis* ability in vitro was calculated by comparison of the level of heavily-infected cells (HIC) in the *Bacillus*-extract treated group compared to the control group that did not contain a *Bacillus* extract. The in vitro Minimum Inhibitory Concentration (MIC) of the *Bacillus* cell-free extracts were measured to assess in vivo sensitivity in a porcine challenge model.

The pathogenic *Lawsonia intracellularis* isolate, GBI06, was collected from a field case in 2006. This strain was grown in a murine fibroblast McCoy cell (CRL 1696, American Type Culture Collection, Virginia US). GBI06 was maintained in a cell culture system as described previously (Guedes and Gebhart, 2003, Comparison of intestinal mucosa homogenate and pure culture of the homologous *Lawsonia intracellularis* isolate in reproducing proliferative enteropathy in swine. Vet. Microbiol. 93, 159-166). The isolate was cultured in a way that demonstrated intracellular as well as extracellular MIC data. The tissue culture system used to demonstrate antimicrobial sensitivity was based on a previous study (Wattanaphansak et al., 2008, Development and validation of an enzyme-linked immunosorbent assay for the diagnosis of porcine proliferative enteropathy. J. Vet. Diagn. Invest. 20, 170-177).

Antimicrobials

Tylosin tartrate (Sigma-Aldrich, Missouri, United States) was used as a control during testing. A stock solution of tylosin tartrate was prepared to a final concentration of 2,560 µg/ml. The tylosin tartrate was dissolved in sterile distilled water. The tylosin tartrate was filter sterilized using a 0.2 µm filter and stored at −20° C. until needed. Two-fold serial dilutions of the stock solution were prepared and working solutions at the following dilutions 1,280, 640, 320, 160, 80, 40, 20, 10, 5, 2.5, and 1.25 µg/ml were produced. The working solutions were further diluted 1:10 by adding 10 µl of antimicrobial stock solution into 90 µl of cell culture media to yield final concentrations of 128, 64, 32, 16, 8, 4, 2, 1, 0.5, 0.25, and 0.125 µg/ml.

Extracellular Testing

Extracellular testing was performed to demonstrate the effect particular antimicrobials have on *Lawsonia intracellularis* prior to entering the host cell. A 96-well plate as shown in Table 2 was inoculated with murine fibroblast McCoy cells and incubated for 24 hours to get approximately 20% confluency. In a second 96-well plate, 100 µl of *Lawsonia intracellularis* cell culture media containing approximately $10^7$ *Lawsonia intracellularis* cells was added to each well. To make dilutions of *Bacillus* supernatants, 100 of supernatant was added to the first row of media containing *Lawsonia intracellularis*. This resulted in the first 1:2 dilution, dilutions were continued 1:2 down the plate to the highest dilution 1:16. Each supernatant dilution series were made in duplicate per plate. Appropriate duplicate tylosin tartrate dilutions were made in duplicate on each plate to achieve the following dilutions (0.125 µg/mL, 0.25 µg/mL, 0.5 µg/mL, 1 µg/mL, 2 µg/mL, 4 µg/mL, 8 µg/mL, 16 µg/mL, 32 µg/mL, 64 µg/mL, and 128 µg/ml). The plates containing dilutions were then incubated at 37° C. with atmospheric conditions of 8.0% oxygen, 8.8% carbon dioxide, and 83.2% nitrogen for 2 hours. These bacterial suspensions were then placed onto the McCoy host cells that were seeded 24 hours prior, and allowed to incubate for another 24 hours. The 96-well plate was then incubated for another 5 days.

TABLE 2 contains a schematic diagram of how plates are organized for intracellular and extracellular assays.

| Antimicrobial Dilution | | | | | | | |
|---|---|---|---|---|---|---|---|
| Supernatant Dilution | *Bacillus* Strain XYZ | *Bacillus* Strain XYZ | *Bacillus* Strain XYZ | *Bacillus* Strain XYZ | *Lawsonia* Control | Tylosin Tartrate | Tylosin Dilution |
| 1:2 | | | | | | | 1:128 |
| 1:4 | | | | | | | 1:64 |
| 1:8 | | | | | | | 1:32 |
| 1:16 | | | | | | | 1:16 |
| 1:2 | | | | | | | 1:8 |
| 1:4 | | | | | | | 1:4 |
| 1:8 | | | | | | | 1:2 |
| 1:16 | | | | | | | 1:1 |

Calculating MIC Value

After the 96-well plates had incubated for 5 days, the supernatant from the infected plates was removed and the cell culture monolayer was fixed with 100 μl of a cold solution containing 50% acetone and 50% methanol for 1 minute. To assess the inhibitory effect of each antimicrobial on *Lawsonia intracellularis* proliferation, the infected plates were strained using a modified immunoperoxidase monolayer assay staining method (Guedes et al., 2002, Validation of an immunoperoxidase monolayer assay as a serologic test for porcine proliferative enteropathy. J. Vet. Diagn. Invest. 14, 528-530).

The *Lawsonia intracellularis* proliferation was evaluated by counting the number of Heavily Infected Cells (HIC) (McOrist et al., 1995, Characterization of *Lawsonia intracellularis* gen. nov, sp nov, the obligately intracellular bacterium of porcine proliferative enteropathy. Int. J. Syst. Bacteriol. 45, 520-525) in each well using an inverted microscope. Host cells were considered to be HIC if the number of intracellular *Lawsonia intracellularis* had proliferated to greater than 30 *Lawsonia intracellularis* bacteria per host cell. The number of HICs in each well was compared as a percentage of the average HICs of the control (non-treated) wells. Cell-free *Bacillus* extracts were considered to have activity against *Lawsonia intracellularis* in vitro if they showed 30% or greater reduction in the number of HICs compared to untreated controls.

Results

Seven different *Bacillus* extracts were identified that had a positive inhibitory effect on *Lawsonia* infection of cells when tested as described above. Out of these, six extracts were retested for activity against *Lawsonia intracellularis* and four out of six extracts had repeatable activity against *Lawsonia intracellularis*.

TABLE 3

| Strain ID | Bacillus Species | In vitro Activity Against Lawsonia |
|---|---|---|
| O52YJ6 | *B. subtilis* | Yes |
| O52YZ5 | *B. subtilis* | Yes |
| O52YYT | *B. amyloliquefaciens* | Yes |
| O22FHD | *B. subtilis* | Yes |
| O72NR7 | *B. pumilus* | Yes |
| O42AH3 | *B. licheniformis* | Yes |
| SB3175 | *B. subtilis* | Yes |
| NRRL B-50015 | *B. licheniformis* | No |

Example 3—Effect on Fecal Score in Piglets Orally Challenged with *Lawsonia intracellularis*

On day −3 of the experiment, 125 three-week old piglets were randomized by weight and gender and divided into 25 pens of 5 animals each. The 25 pens were randomized into 5 treatment groups with 5 pens each. Animals in three groups were then put on a standard diet, while animals in another group were put on the standard diet to which $1\times10^{12}$ colony-forming units (CFU) of spores of *Bacillus subtilis O*52YJ6 had been added (O52YJ6 group). Animals in the remaining group received the same diet as in group O52YJ6 except that spores of *Bacillus pumilus* 3002 were used instead of *B. subtilis O*52YJ6 (group 3002). All diets were fed throughout the entire experiment to the same animals.

On day 0, all animals from one group on the standard diet were vaccinated orally with the Enterisol vaccine from Boehringer Ingelheim according to the manufacturer's instructions (vaccine or VAC group). Another group on the standard diet did not receive any further treatment or challenge (negative control or NC group). The remaining group will be referred to as positive control or PC group.

On day 21, all animals, except those in the NC group, received an intragastric gavage with a homogenate of pig intestinal mucosal tissue that contained large numbers of the intracellular pathogenic bacterium *Lawsonia intracellularis*, the causal agent of proliferative enteropathy (PE).

On day 42 all animals were euthanized and examined for signs of PE. Fecal appearances were scored per pen on days 20, 28, 31, 35, 38. For each pen, a score of 0 was attributed when the majority of fecal matter had a normal appearance. A score of 1 was attributed when fecal matter was mainly soft, with a cow-pie consistency. A score of 2 meant that fecal matter was moderately loose and fell through the slats of the floor. A score of 3 was assigned when the majority of fecal matter was watery, possibly blood-tinged, possible necrotic debris.

Blood samples were taken from each animal on days 0, 20 and 42.

TABLE 4

| | 0 | 1 | 2 or 3 |
|---|---|---|---|
| PC | < | > | > |
| VAC | > | < | < |
| O52YJ6 | < | > | < |

TABLE 4-continued

|  | 0 | 1 | 2 or 3 |
|---|---|---|---|
| 3002 | < | > | > |
| NC | > | < | < |

Xhi-square test of cumulative fecal scorings in each group. A < symbol indicates that a treatment had less frequently a certain score than could be expected if none of the treatments had any effect. The sign > indicates increase in occurrence. Table 4 shows that animals in the O52YJ6 group had less often a score of 2 or 3 than animals in the PC group.

Results

As shown in FIG. 1, animals in group 1 produced mainly fecal matter over the course of the experiment that was of normal appearance (score 0). Only 3% of cases had a score higher than 0. Animals in the PC group had the most often scores superior to 0. A Chi square test, of which the results are in table 4, indicates that animals in the O52YJ6 group had less often a fecal score of "3" than animals in the PC group, suggesting that ingestion of *Bacillus subtilis* O52YJ6 could protect animals from developing severe diarrhea upon challenge with *Lawsonia intracellularis*.

Example 4—Effect on Growth and Immune Responses in Piglets Orally Challenged with *Lawsonia intracellularis*

General

A total of 60 newly weaned piglets (age 21 days) was randomized by weight and gender over 5 treatments groups, as follows:
1. Control group (N=10). Animals received standard diet throughout the experiment and were not challenged with *Lawsonia intracellularis*;
2. Challenged, untreated group (N=20). Animals received standard diet throughout the experiment and were challenged at age 52 days via intragastric gavage with *Lawsonia intracellularis* homogenate (approximately $2.0 \times 10^7$ bacteria/dose) diluted into 40 mL of sterile carrier buffer;
3. O42AH3 group (N=10). Animals received standard diet to which had been added $1 \times 10^{\wedge}12$ CFU of spores of *Bacillus licheniformis* strain O42AH3 from weaning till slaughter and were challenged at age 52 days with *Lawsonia intracellularis*;
4. O72NR7 group (n=10). As group 3, except that *Bacillus pumilus* O72NR7 was used instead of *B. licheniformis* O42AH3;
5. O52YYT group (n=10). As group 3, except that *Bacillus amyloliquefacines* O52YYT was used instead of *B. licheniformis* O42AH3.

Effect on Bodyweight Gain

Bodyweights were individually determined at age 21 days, 52 days (immediately before challenge), and immediately before euthanasia and necropsy at day 70, and average daily gains (ADG) were determined for the pre-challenge period, post-challenge period, and entire period, by dividing weight gains (in grams) over the respective periods by the number of days in that period.

Figure 2:
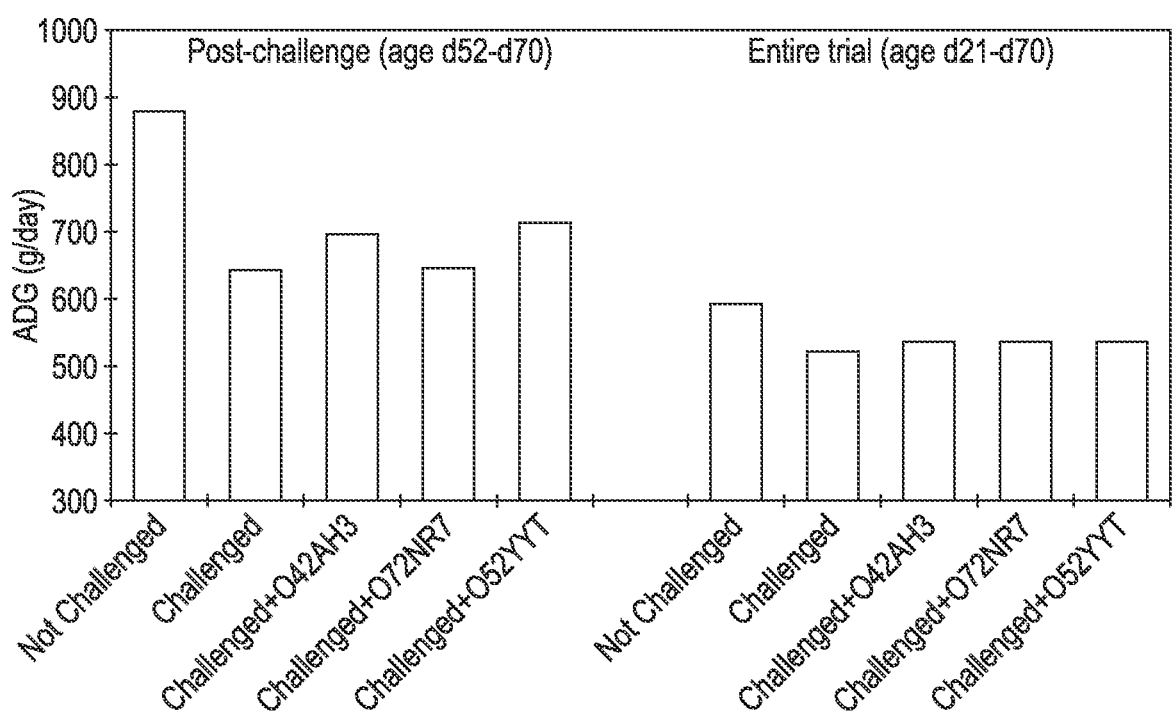
FIG. 2 shows the effect of feeding piglets a diet enriched with $1 \times 10^{12}$ CFU probiotics/ton from weaning (age 21 days) to slaughter (age 70 days) on average daily gain (ADG). "Challenged" indicates that all animals in that group received an oral challenge with *Lawsonia intracelluaris* (approximately $2.0 \times 10^{7}$ bacteria/dose) at age 52 days.

As seen in FIG. 2, all animals challenged with *Lawsonia intracellularis* had a significantly lower ADG post-challenge than animals in group 1 (no-challenge), indicating that the challenge with *Lawsonia intracellularis* had, as predicted, a negative impact on growth performance. However, animals receiving O42AH3 (Group 3) or O52YYT (Group 5) had a higher ADG than challenged animals without treatment (Group 2). For O42AH3 and O52YYT the increases in ADG versus untreated were 8.7% and 10.8% respectively. O72NR7 showed an improvement of 0.4%. Taking into account the entire experimental duration, all three probiotics had higher ADG than challenged animals with no treatment (2.7, 3.1 and 3.1% for O42AH3, O72NR7 and O52YYT, respectively).

*Lawsonia intracellularis* Infectivity

To test the ability of the *Bacillus* strains O42AH3, O72NR7 and O52YYT to inhibit infectivity of *Lawsonia intracellularis*, we measured two parameters: 1) Levels of Immunoglobulin G (IgG) in the serum of piglets from groups 1-5 obtained after slaughter and 2) the number of *Lawsonia intracellularis* cells per gram feces obtained at various time point after challenge.

Effect on Seroconversion

Figure 3:
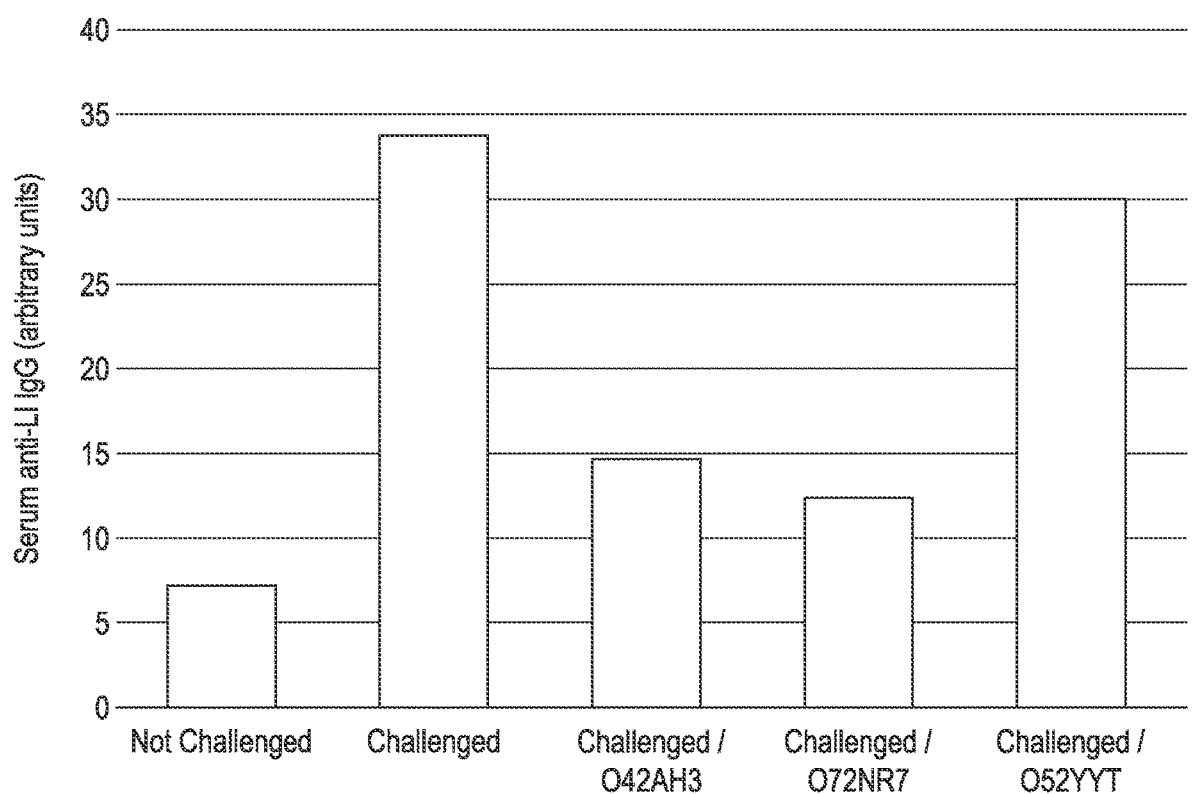
FIG. 3 shows anti-*Lawsonia intracellularis* IgG in sera obtained at slaughter, i.e. 18 days after oral challenge with *Lawsonia intracellularis*. All probiotics, but especially O42AH3 and O72NR7, resulted in lower IgG responses, suggesting a protective effect against *Lawsonia intracellularis*.
Figure 4:
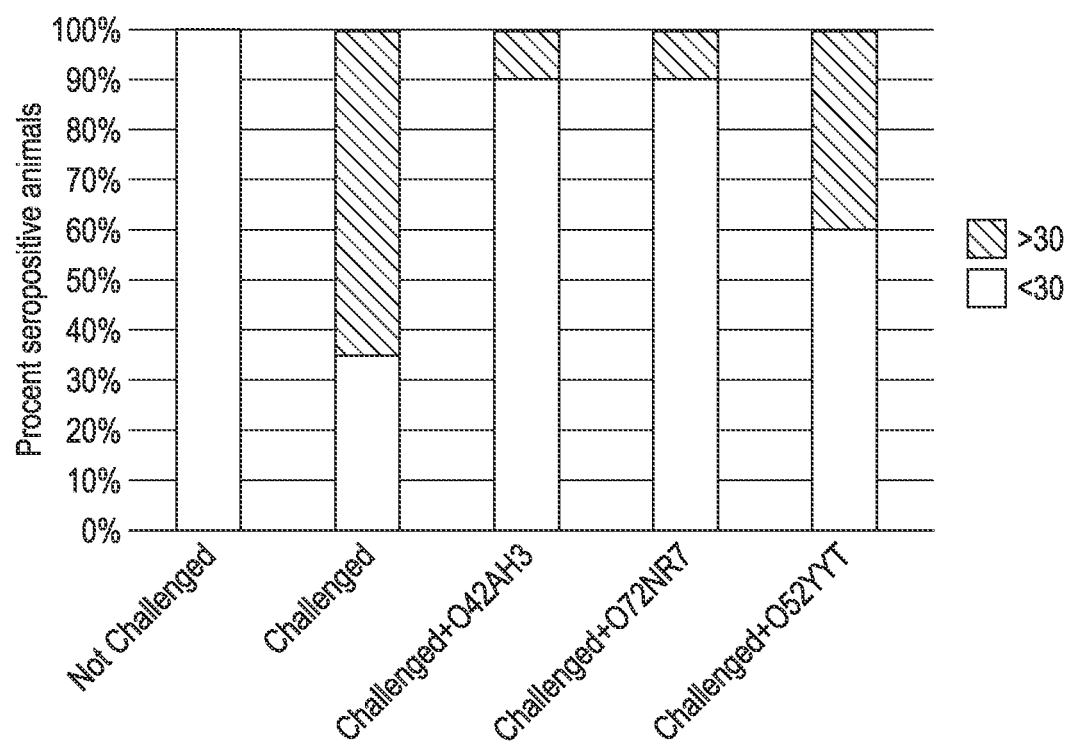
FIG. 4 shows percent animals being sero-positive for *Lawsonia intracellularis* at the end of the experiment, i.e. percentage of animals having ELISA values >30 at day 70 of age following an oral *Lawsonia intracellularis* challenge at age 52 days.

An ELISA was used to measure IgG against extracts of whole *Lawsonia intracellularis*. A readout of 0-20 indicates a negative test; a readout of 20-30 indicates borderline seropositivity; a readout >30 means the animal is seropositive for anti-*Lawsonia intracellularis* IgG and has developed infection. As shown in FIG. 3, it was observed that piglets receiving a diet containing O42AH3, O72NR7, or O52YYT before from weaning till slaughter all had lower average numbers of anti-*Lawsonia intracellularis* IgG in their serum than animals in group 2, indicating that all three *Bacillus* strains were able to limit infectivity of *Lawsonia intracellularis*. In FIG. 4, the results are also expressed as the fraction of animals per group that is sero-positive, i.e. of which the ELISA values exceeded 30.

Effect on Fecal *Lawsonia intracellularis* Shedding

Figure 5:
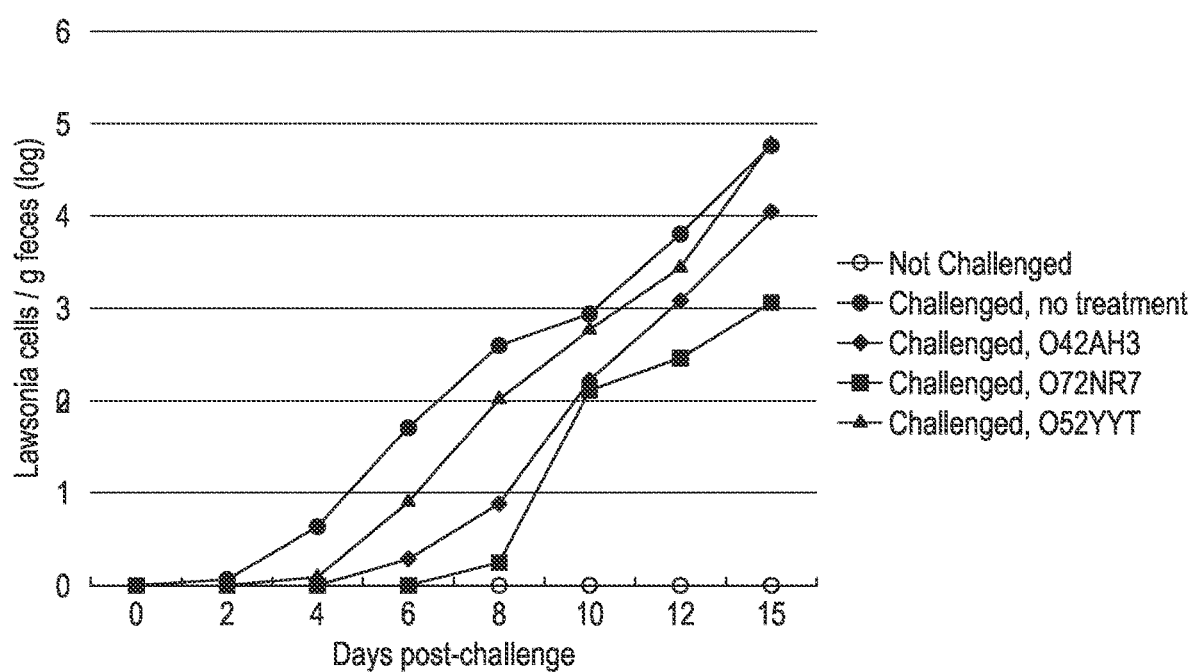
FIG. 5 shows the effect of probiotics on fecal *Lawsonia intracellularis* shedding.

Fecal samples were obtained from all animals in all groups, immediately before the oral challenge (post-challenge day 0), and on days 2, 4, 6, 8, 10, 12 and 15 post-challenge. DNA was isolated from the feces and the amount of DNA belonging to *Lawsonia intracellularis* was quantified with real-time PCR. The use of a standard curve plotting Ct values versus those obtained with known amounts of DNA allowed us to calculate the number of *Lawsonia intracellularis* bacteria per gram feces. As shown in FIG. 5, non-challenged animals (Group 1) had no detectable *Lawsonia intracellularis* DNA in their feces at any time point, whereas all challenged animals started to shed significant amounts of *Lawsonia intracellularis* at the latest by day 8 post-challenge. Animals in groups 3, 4 and 5 shed lower amounts of *Lawsonia intracellularis* than animals in group 2 (area under the curves) and the time of onset of shedding was also delayed compared to group 2 (FIG. 5). Thus, inclusion of one of either of the three strains of *Bacillus* in the diet limited shedding of *Lawsonia intracellularis* in the feces, suggesting that *Lawsonia intracellularis* replication in animals on these diets was impaired.

Pathology

Figure 6:
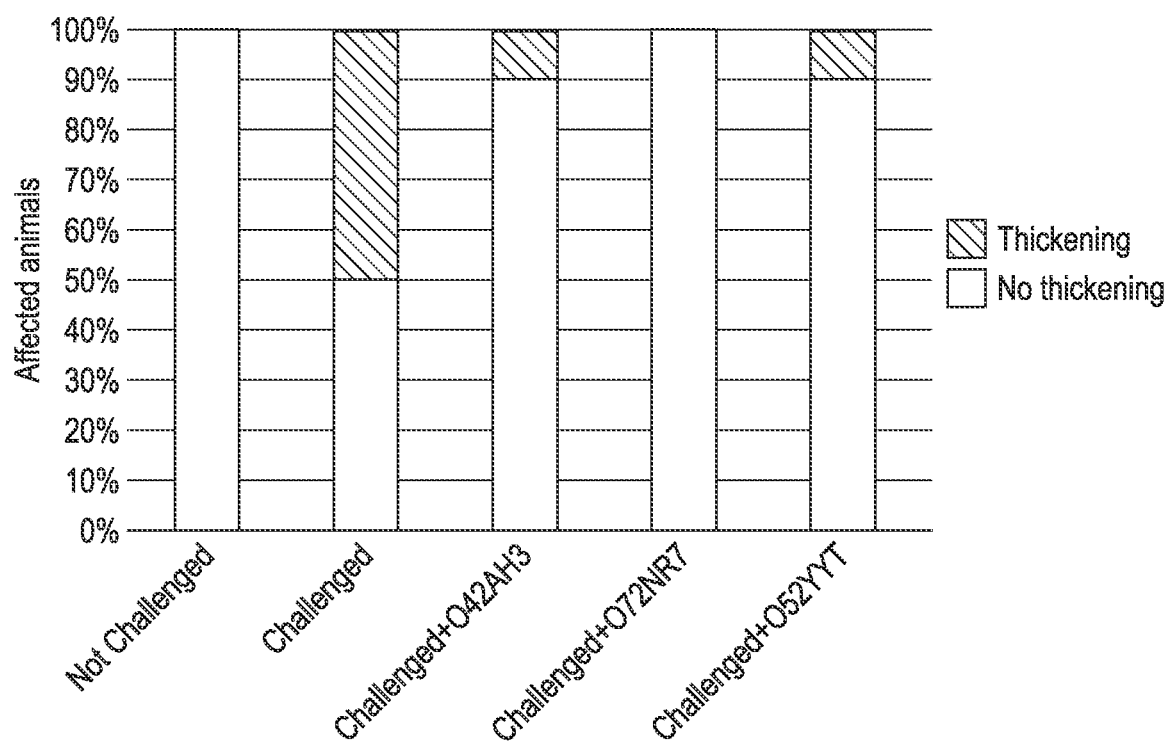
FIG. 6 shows macroscopic thickening in the small intestine. White parts of each bar indicate the fraction of piglets with no thickening at necropsy, shaded parts of bars indicate the fraction of animals with thickening.

Since piglets with either of the three probiotics in the diet showed decreased fecal *Lawsonia intracellularis* shedding and reduced immune responses to *Lawsonia intracellularis* upon *Lawsonia intracellularis* challenge compared to non-treated challenged animals, we hypothesized that these probiotics would also reduce intestinal pathology due to infection with *Lawsonia intracellularis*. To this end, macroscopically visible thickening of the small intestine, a hallmark of PE (Vannucci, F. A., & Gebhart, C. J. (2014). Recent advances in understanding the pathogenesis of *Lawsonia intracellularis* infections. *Vet. Pathol.*, 51, 465-477) was scored with a semi-quantitative scale, with "0" representing no thickening and "3" presenting most severe thickening. FIG. 6 represents the distribution of animals with no or only minor thickening (scores 0, 1) versus animals with mild or severe thickening (scores 2, 3) for each group.

The results indicate that all tree probiotics were able to reduce small-intestinal thickening after the *Lawsonia intracellularis* challenge compared to untreated, *Lawsonia intracellularis*-challenged animals.

Figure 7:
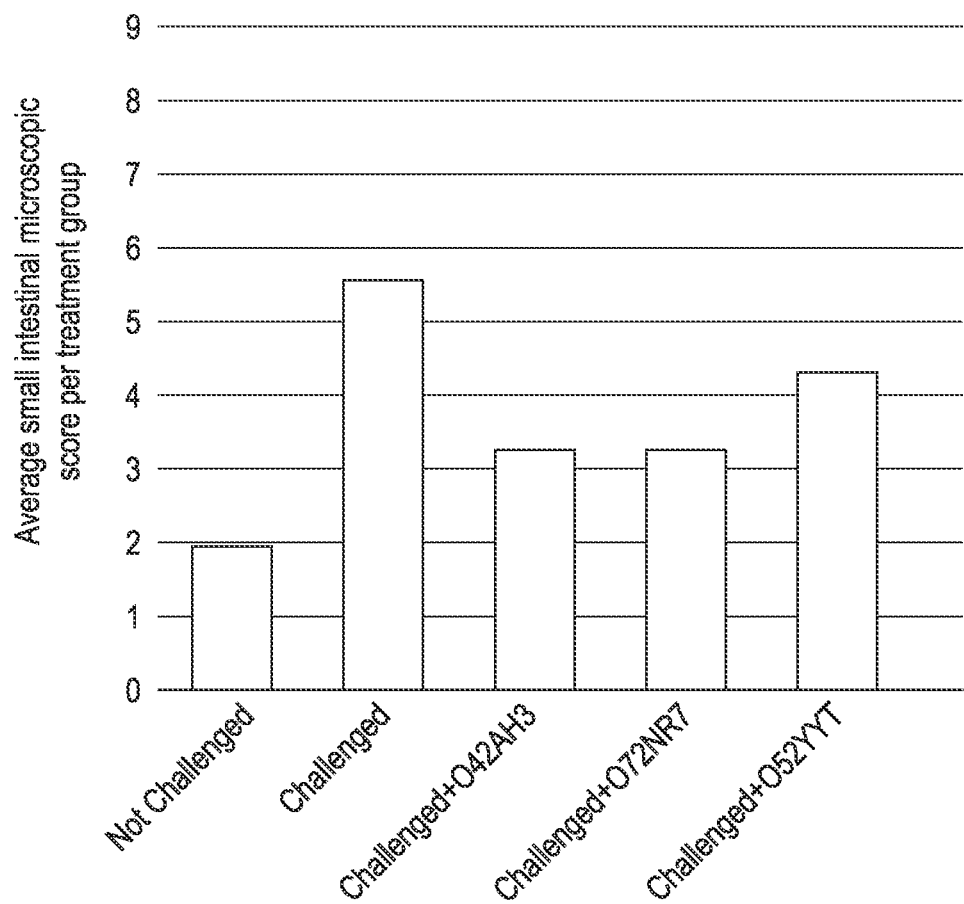
FIG. 7 shows average small intestinal microscopic scores per treatment group. All three probiotics reduced infection scoring after *Lawsonia intracellularis* challenge compared to non-treated animals.

For each animal also a sum of scores of several microscopic parameters of PE was established. The individual components that were scored were as follows: Thickening of crypts and villi (0=no thickening; 3=worst thickening); microscopic scoring of lymphohistiocytic infiltration (0=non; 3=worst); and microscopic assessment of inflammation (0=non; 3=worst). Animals with a score of 9 had been severely affected, a score of 0 indicated absence of signs of disease. Results, shown in FIG. 7, showed that all three probiotics resulted in lower small intestinal microscopical inflammation upon challenge than untreated challenged animals.

Example 5—Effect on Growth and Immune Responses in Piglets Naturally Challenged with *Lawsonia intracellularis*

General:

A total of 1728 weaned piglets, obtained by breeding Large White×Landrace-type sows (Topigs 40) with Duroc-type boars (Topigs Talent)), average age of 28 days, were randomized over 4 treatments.

Treatment 1 (Tx1) received a standard diet (mainly wheat, barley and corn during post-weaning and mainly wheat and corn during fattening).

Tx2 received the same diet but piglets were vaccinated with Enterisol (Boehringer Ingelheim) per os at weaning as per the manufacturer's instructions.

Tx3 and Tx4 were not vaccinated and received the same diets as Tx1 and Tx2, to which was added $1\times10^{12}$ CFU/ton NZ014 (Tx3) or $1\times10^{12}$ CFU/ton O72NR7 (Tx4).

Respective diets were administered from weaning till slaughter. Animals, balanced for bodyweight and gender, were randomized to one of these four treatment groups spread over 8 rooms in the nursery building and over 4 rooms in the fattening building.

Effect on Bodyweight Gain

Bodyweight and feed intake were determined per pen on the start of the study (average age: 28 days), at age 42 d, 70 d, 135 d and 165 d. Bodyweights (BW) of deceased animals were noted at the day of death. Average daily gain ("ADG", in g/day) and feed conversion rate ("FCR"; daily feed intake/ADG) were calculated for the nursery phase as a whole (d28–d70) or for the fattening phase as a whole (d70–d165).

Figure 8A:
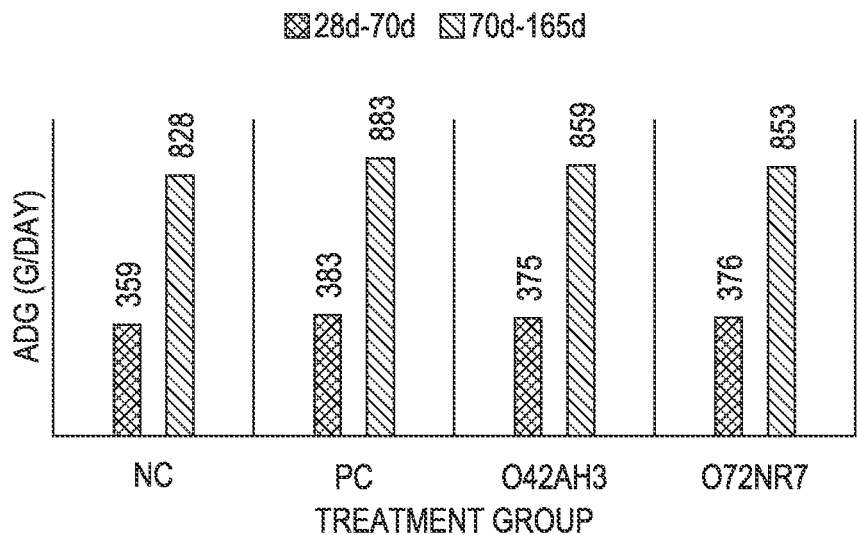
FIGS. 8A and 8B show the effect of feeding weaned piglets different diets in a farm having presence of *Lawsonia intracellularis*, where the effect is measured on average daily gain ("ADG", in g/day) and feed conversion rate ("FCR" in g/day; daily feed intake/ADG) calculated for the nursery phase as a whole (28 days-70 days) or for the fattening phase as a whole (70 days-165 days). NC ("negative control") refers to animals receiving standard diet; PC to animals on standard diet but who were all vaccinated with Enterisol within a week of weaning; O42AH3 and O72NR7 refers to groups of animals receiving standard diet to which the respective *Bacillus* strains had been added at an inclusion rate of $1 \times 10^{12}$ CFU/ton feed.
Figure 8B:
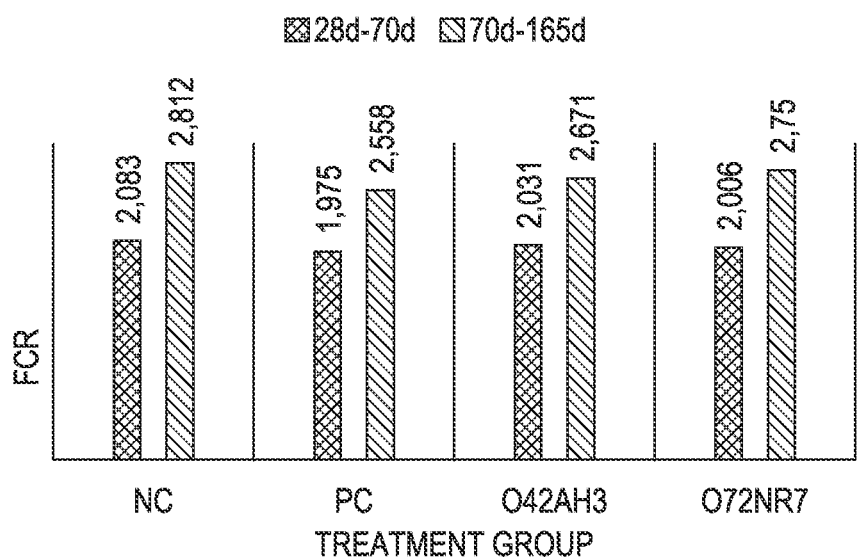
Figure 9:
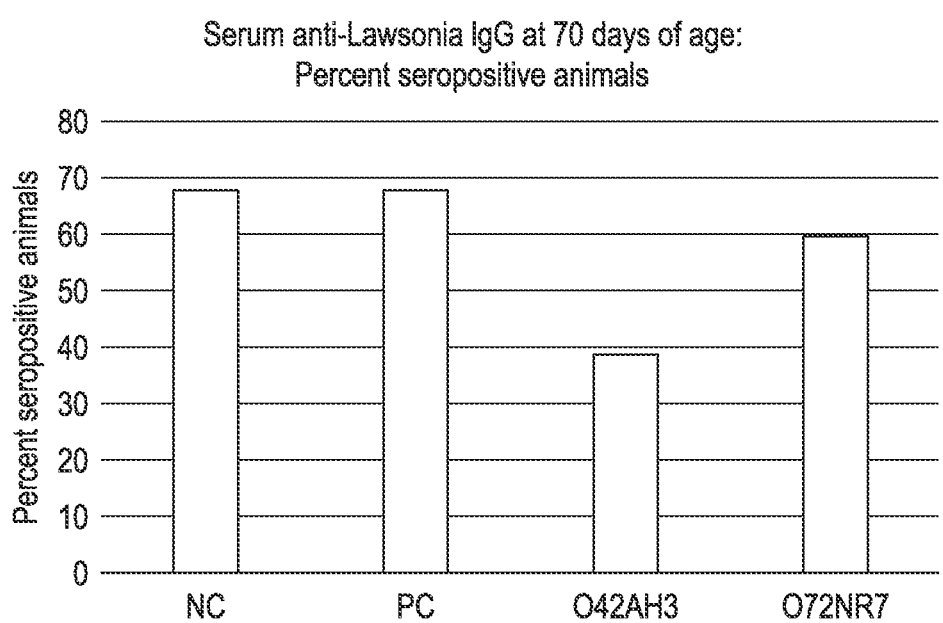
FIG. 9 shows anti-*Lawsonia intracellularis* IgG in sera obtained at day 70 of piglets receiving different diets in a farm having presence of *Lawsonia intracellularis*. NC ("negative control") refers to animals receiving standard diet; PC to animals on standard diet but who were all vaccinated with Enterisol within a week of weaning; O42AH3 and O72NR7 refers to groups of animals receiving standard diet to which the respective *Bacillus* strains had been added at an inclusion rate of $1 \times 10^{12}$ CFU/ton feed.

In FIG. 8, NC ("negative control") refers to animals receiving standard diet; PC to animals on standard diet but who were all vaccinated with Enterisol within a week of weaning; O42AH3 and O72NR7 refers to groups of animals receiving standard to which the respective *Bacillus* strains had been added at an inclusion rate of $1\times10^{12}$ CFU/ton feed.

As evident from FIG. 8, compared to untreated control animals ("NC" group), animals vaccinated with Enterisol or animals with either O42AH3 or O72NR7 in their diet showed significantly increased average daily gains (ADG) and significantly improved feed conversion rates (FCR) over all time periods tested. From day 28 of age till age 70, considered the nursery stage, ADG improvements of the Enterisol (PC) group, O42AH3 group, and O72NR7 group, all versus the negative control (NC) group, were 6.7%, 4.5% and 4.7%, respectively. Corresponding FCR improvements were 5.2%, 2.5% and 3.7%. From age 70 till age 165, considered the fattening phase in pig production, improvements in ADG versus NC groups were 6.6% for the PC group, 3.8% for the O42AH3 group, and 3.0% for the O72NR7 group, respectively. Corresponding improvements in FCR were 9.1, 5.0, and 2.2%, respectively.

Effect on Development of Anti-*Lawsonia intracellularis* IgG

Blood samples were collected at age 70 days from 3 randomly chosen pigs per pen for detection of anti-*Lawsonia intracellularis* IgG by ELISA (Svanova Bioscreen). An animal's serum was considered seropositive according to the manufacturer's instructions.

As shown in figure xxx, the percentage animals in the O42AH3 and the O72NR7 groups testing seropositive for *Lawsonia* was reduced compared to the percentage seropositive animals in the NC group. Thus, adding O42AH3 or O72NR7 to the diet had reduced the infectivity of *Lawsonia intracellularis*.

Example 6—Effect on Growth and Fecal Shedding in Piglets Orally Challenged with *Lawsonia intracellularis*

General

This trial was conducted on a commercial farm in Korzekwice, Poland, from December 2017-October 2018. Presence of *Lawsonia intracellularis* on the farm was confirmed by serological analysis.

A total of 768 weaned male and female piglets, average age of 28 days, were randomized over 4 treatments.

Treatment 1 (Tx1; negative control "NC")) received a standard diet (mainly wheat, barley, soy meal).

Tx2 (positive control; "PC") received the same diet but piglets were vaccinated with Enterisol (Boehringer Ingelheim) per os at weaning as per the manufacturer's instructions.

Tx3 and Tx4 were not vaccinated and received the same diet as Tx1 and Tx2 but supplemented with $1\times10^{12}$ CFU/ton O52YYT (Tx3) or $1\times10^{12}$ CFU/ton O72NR7 (Tx4), respectively, from weaning till slaughter.

Animals, balanced for bodyweight and gender, were randomized to one of these four treatment groups.

Effect on Bodyweight Gain

Bodyweight and feed intake were determined per pen on the start of the study (average age 28 days; start of nursery phase), at age 45 d, 88 d (end of nursery phase), 147 d, and 207 d. Bodyweights (BW) of deceased animals were noted at the day of death. Average daily gain ("ADG", in g/day or kg/day), average daily feed intake ("FI" in g/day) and feed conversion rate ("FCR"; FI/ADG) were calculated for each period as well as for the nursery phase as a whole (d28–d78), for the fattening phase as a whole (d88–d207), and for the entire post-weaned lifespan of the animals.

Figure 10A:
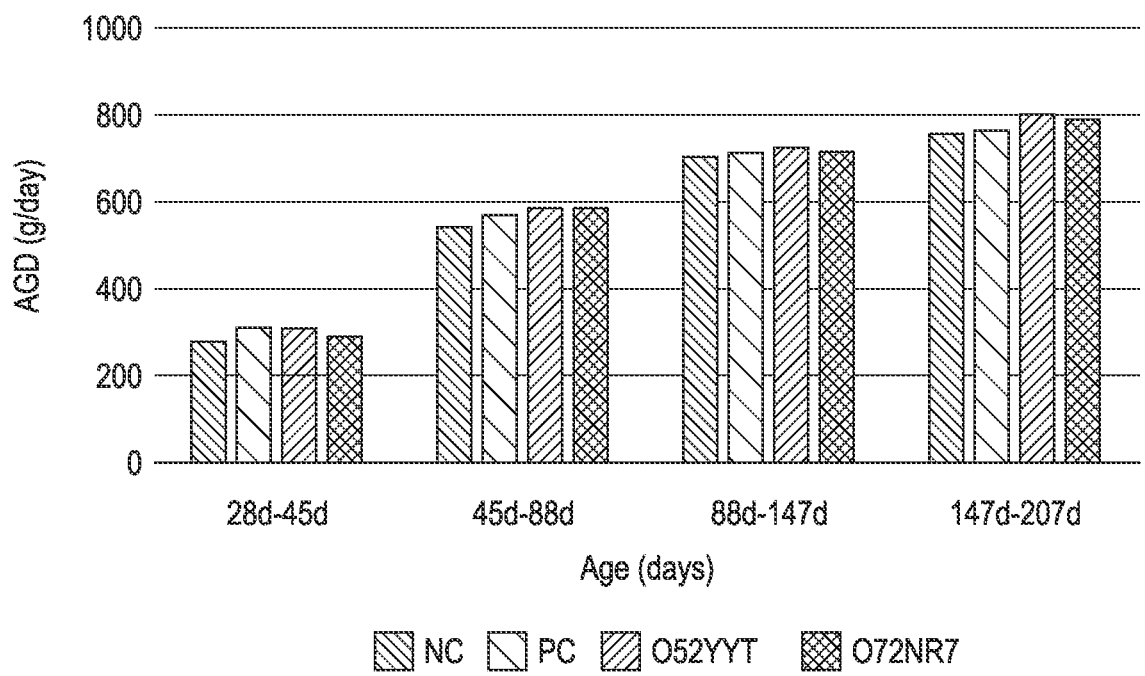
FIGS. 10A and 10B show the effect of feeding weaned piglets different diets in a farm having presence of *Lawsonia intracellularis*, where the effect is measured on average daily gain ("ADG", in g/day) and feed conversion rate ("FCR" in g/day; daily feed intake/ADG) calculated for the following phases 28 days-45 days, 45 days-88 days, 88 days-147 days and 147 days-207 days. NC ("negative control") refers to animals receiving standard diet; PC to animals on standard diet but who were all vaccinated with Enterisol within a week of weaning; O52YYT and O72NR7 refers to groups of animals receiving standard diet to which the respective *Bacillus* strains had been added at an inclusion rate of $1 \times 10^{12}$ CFU/ton feed.
Figure 10B:
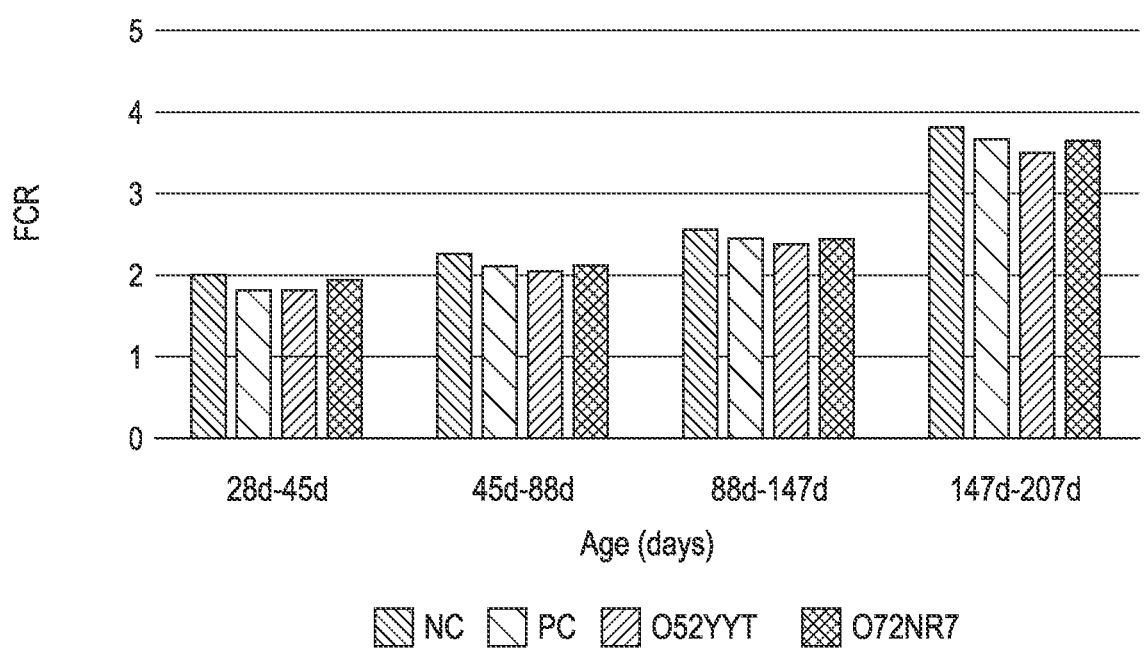

Results in FIG. 10 show that, on average, animals in the positive control group (PC; all animals in this group were vaccinated with Enterisol within a week from weaning) showed improved ADG and FCR compared with animals in the negative control group (NC) for all time periods tested, including the entire nursery phase (age day 28–day 88) and the entire fattening phase (age day 88 days–207). Animals with O72NR7 in their diet also had significantly improved ADG and FCR in the nursery phase and in the fattening phase compared to animals in the NC group. The same was observed for animals with O52YYT in their diet.

Effect on Fecal *Lawsonia intracellularis* Shedding

Rectal fecal samples were obtained from two randomly selected animals per pen at day 88 and 147 and *Lawsonia intracellularis* DNA in the samples was identified by realtime PCR using the "Amplitest" *Lawsonia intracellularis* realtime PCR assay from Amplicon Inc. (Wroclaw, Poland).

Figure 11:
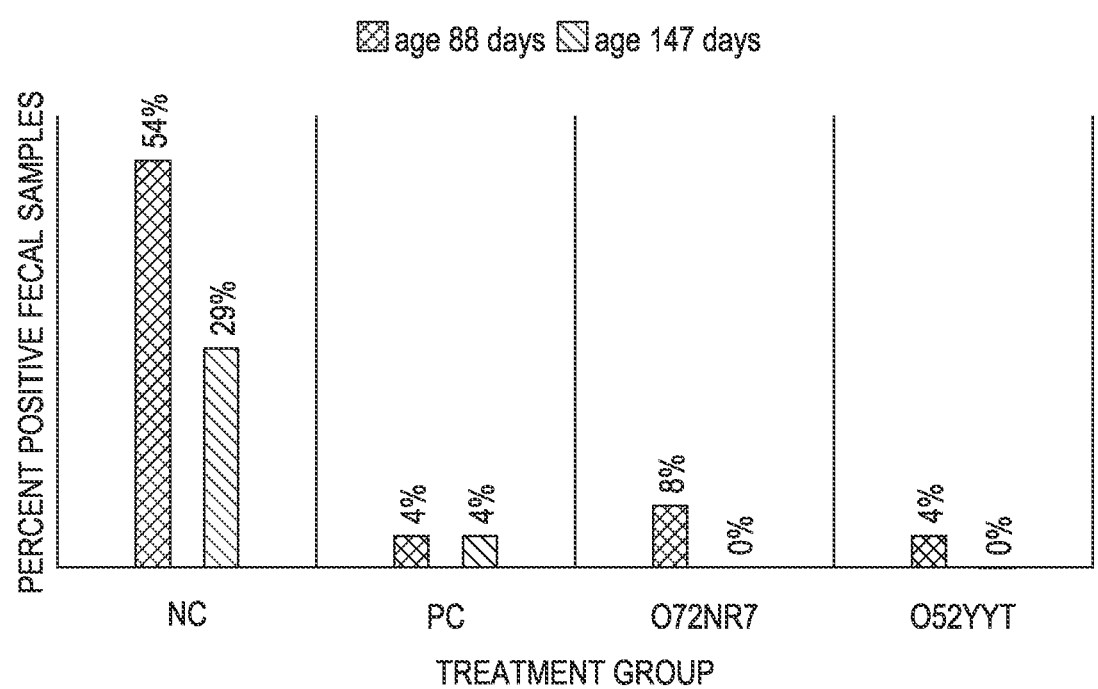
FIG. 11 shows the effect of probiotics on fecal *Lawsonia intracellularis* shedding at day 88 and 147 of piglets receiving different diets in a farm having presence of *Lawsonia intracellularis*.

As shown in FIG. 11, animals vaccinated with Enterisol (PC group) or animals receiving either O72NR7 or O52YYT in their diet shed significantly less *Lawsonia intracellularis* in their feces, indicating that dietary enrichment with O72NR7 or O52YYT reduced the presence of *Lawsonia intracellularis* in their digestive tract.

Example 7: Trans-Epithelial Electrical Resistance of *Bacillus*

Trans-epithelial electrical resistance (TEER) was used as an in vitro model for the strength of the intestinal barrier function. The greater the electrical resistance, the stronger the barrier function.

Method

In a transwell system, polarized Caco-2 cells were stimulated with either bacteria alone, inflammation conditions alone (TNFalpha, INFgamma), or with both bacteria and inflammation. TEER was recorded every hour over a period of 48 hours. Data was normalized to the average of 6 hours prior to stimulation. Technical duplicates were performed per experiment.

Figure 12:
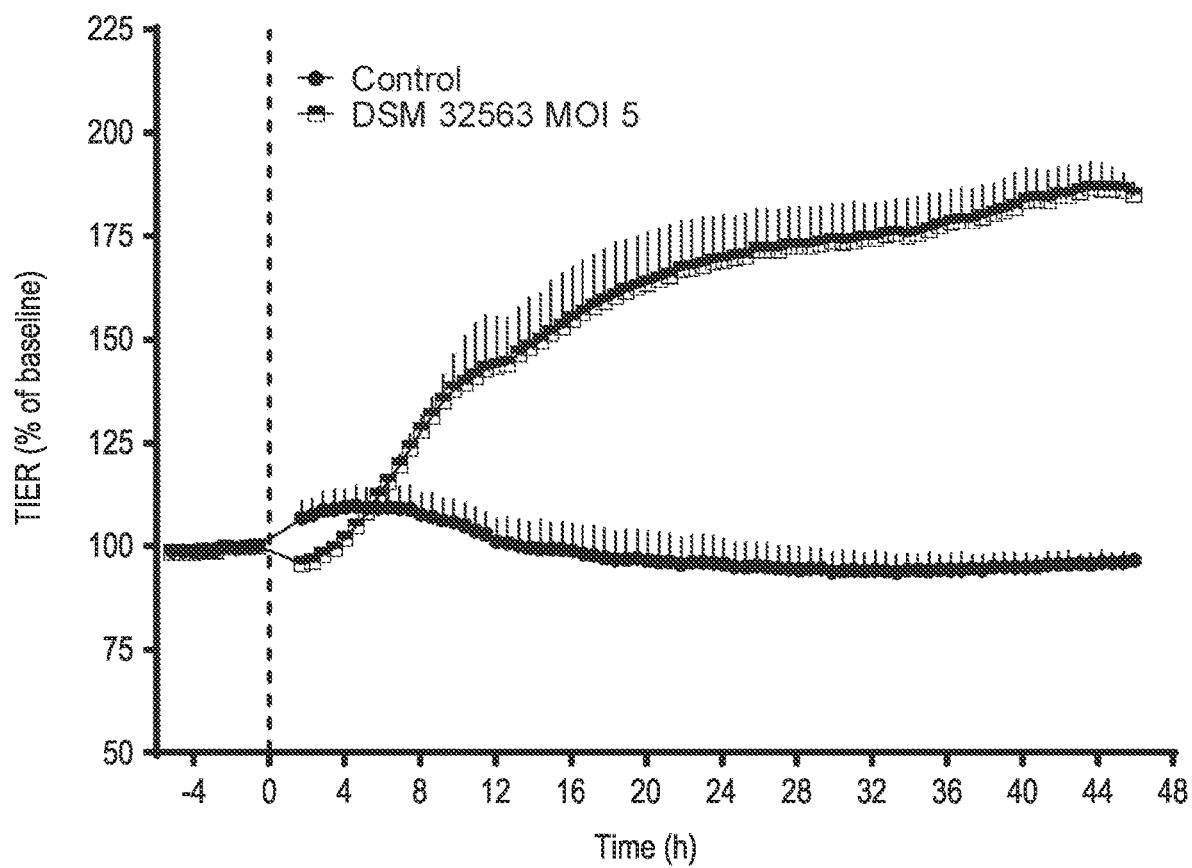
FIG. 12 shows TEER results comparing DSM 32563 (O72NR7) vs. control without inflammatory conditions at a Multiplicity Of Infection (MOI) of 5.
Figure 13:
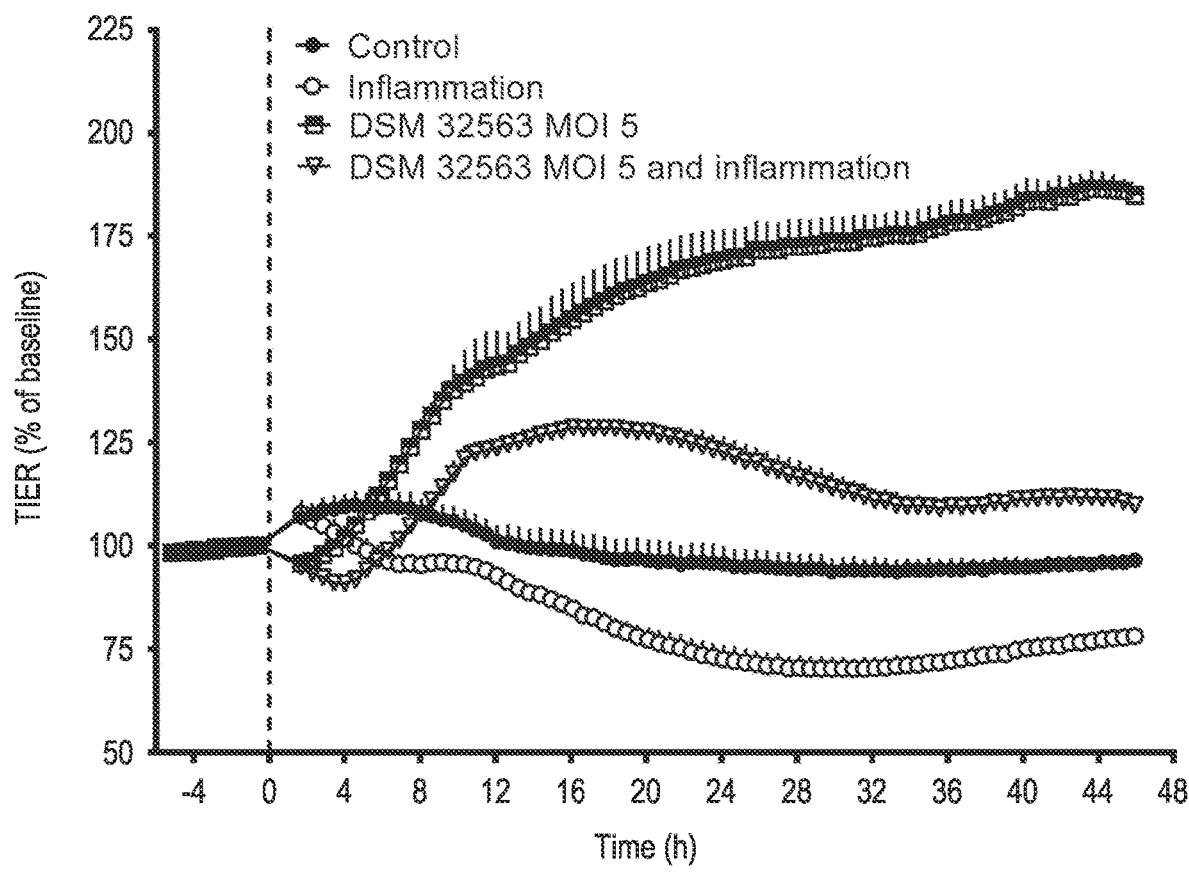
FIG. 13 shows that DSM 32563 (O72NR7) rescued the inflammation-dependent drop in TEER seen with inflammatory conditions caused by TNFalpha and INFgamma at a Multiplicity Of Infection (MOI) of 5.

Results:

O72NR7 (DSM 32563) caused a prolonged increase in TEER values, indicating a strengthening of the barrier function in vitro, compared to control cells (FIG. 12). Inflammatory conditions often cause a drop in TEER, indicating a weakened barrier function. With O72NR7 (DSM 32563) tested under inflammatory conditions, the TEER values were rescued compared to the control or the control+ inflammation groups (FIG. 13).

Example 8: Microbiome Sequencing and Analysis

Sample Collection

Rectal swabs were collected from a single animal per pen and preserved in sterile phosphate buffer. After soaking, swabs were discarded and the remaining material dissolved in phosphate buffer frozen for storage at −80° C. Material was later used for DNA extractions. A total of 96 samples were collected.

DNA Extractions Using the Powerlyzer Powersoil DNA Extraction Kit 250 ul of the buffer from the swab sample was placed into a PowerBead Tube and 750 ul of Powerbead Solution was added to the PowerBead Tube. 60 ul of Solution C1 was added and inverted several times or vortexed briefly. The PowerBead Tubes were secured onto the FastPrep system and shook at 1600 rpm for 60 seconds. The bead tubes were centrifuged at 10,000 rcf for 1 minute. 450 ul of the supernatant were transferred to a clean 2 ml Qiacube collection cuvette and the Qiacube was set up according the Protocol instructions for Powerlyzer Powersoil kit and the protocol was run accordingly. Once extraction was complete, DNA samples were frozen in cryovials and stored at −80° C. until ready to use.

Sequencing and Analysis

DNA extraction, PCR amplification of the 16S RNA gene and library construction:

PCR amplification was done according to Phusion.Pcrl with 20 cycles. DNA was measured using the HS kit for quantification. Post-PCR cleanup was done according to the protocol below.

Montage PCR Clean Up:

5 ul from each PCR were removed and pooled in a DNA LowBind Eppendorf tube. 300 μl of the pooled sample was added on the filter part of Montage tubes and centrifuged in Montage tubes at 3000 G for 25 min. The Montage tube with supernatant was discarded. The filter part of the Montage tubes was kept and placed in new Montage tubes. 20 μl of elution buffer-10 mM Tris-HCl pH 8 was added on the filter part of the Montage tubes and mixed using a pipette. The filter part was turned upside-down in new Montage tubes, then the sample was centrifuged in Montage tubes at 2000 G for 5 min. Finally, the supernatant was transferred to DNA LowBind Eppendorf tubes.

Bioinformatics Processing, OTU Clustering and Classification

The generation of Operational Taxonomic Unit (OTU) tables was done with usearch version 10.0.240 (UNOISE2: improved error-correction for Illumina 16S and ITS amplicon sequencing:

www.biorxiv.org/content/early/2016/10/15/081257).

Primer binding regions were removed with fastx_truncate and reads were filtered to contain less than one error per read. The quality filtered reads were denoised with unoise3. OTU abundance was calculated by mapping with usearch_global using a 97% identity threshold. Taxonomical classification was done with the RDP classifier version 2.12. The phylogentic tree was made by aligning the 16S sequences with mafft and the tree was inferred by FastTree.

Statistical Analysis

The results were analyzed in R using the ampvis package v.1.9.1 (Albertsen et al., 2015, Back to basics the influence of DNA extraction and primer choice on phylogenetic analysis of activated sludge communities. PLoS One. 2015 Jul. 16; 10), which builds on the R package DESeq2 (Love et al., 2014. Moderated estimation of fold change and dispersion for RNA-seq data with DESeq2, Genome Biology 15(12): 550) for detecting species in differential abundance. Beta diversity was analyzed by calculating Unifrac distances. Variance analysis of beta diversity was done with adonis (Permutational multivariate analysis) from the vegan package.

Results

Animals in both the *Bacillus licheniformis* strain O42AH3 and *Bacillus pumilus* strain O72NR7-fed groups showed several changes to the intestinal bacterial community as determined by comparisons of relative abundance. Here, relative abundance indicates the proportion of individual sequence reads in an individual animal sample that corresponds to a known and identified taxonomic group, compared to all sequence reads in the same sample. In both O42AH3 and O72NR7-fed animals there was a reduction in the overall level of members of the phylum Proteobacteria, compared to controls (Table 5).

TABLE 5

Relative abundance, expressed as a percentage, of the phylum Proteobacteria in different treatment groups.

| Treatment | Percentage of relative abundance of Proteobacteria |
| --- | --- |
| Control | 14.1 |
| Enterisol vaccine | 5.5 |
| *Bacillus licheniformis* strain O42AH3 | 4.1 |
| *Bacillus pumilus* strain O72NR7 | 2.3 |

Within the phylum Proteobacteria, several genera were reduced in both O42AH3 and O72NR7-fed animals, compared to the control. These included the genus *Escherichia/Shigella*, *Campylobacter*, *Burkholderia*, and *Acinetobacter* (Table 6).

TABLE 6

In the phylum Proteobacteria, several specific genera had reduced relative abundance in Bacillus-fed treatment groups compared to the control or Enterisol.

| Treatment | Escherichia/Shigella | Campylobacter | Burkholderia | Acinetobacter |
|---|---|---|---|---|
| Control | 4.2 | 3 | 2.1 | 10.1 |
| Enterisol | 3.8 | 3.7 | 2 | 0 |
| O42AH3 | 2.2 | 2.5 | 1.6 | 0.1 |
| O72NR7 | 2 | 0.7 | 0.7 | 0.2 |

Additionally, several members of the intestinal community had higher relative abundance in O42AH3 and/or O72NR7-fed animals, including members of the genus *Ruminococcus, Blautia, Lactobacillus, Megasphaera* and *Faecalibacterium* (Table 7).

TABLE 7

Some specific genera were increased in relative abundance in Bacillus-fed treatment groups compared to the control or Enterisol.

| Treatment | Lactobacillus | Megasphaera | Faecalibacterium | Ruminococcus | Blautia |
|---|---|---|---|---|---|
| Control | 10.1 | 0.3 | 0.6 | 0.7 | 0.5 |
| Enterisol | 31.1 | 1.2 | 1.3 | 1.2 | 0.7 |
| O42AH3 | 20.5 | 2.6 | 1.5 | 1.2 | 0.7 |
| O72NR7 | 34 | 3.7 | 2.9 | 1.4 | 1.3 |

Example 9: Animal Feed and Animal Feed Additives Comprising a *Bacillus* Strain Animal Feed Additive A formulation comprising the *Bacillus* strain of the invention (e.g. *Bacillus licheniformis* O42AH3 (deposit no. DSM 32559), *Bacillus subtilis* O52YJ6 (deposit no. DSM 32560), *Bacillus amyloliquefaciens* O52YYT (deposit no. DSM 32561), or *Bacillus pumilus* O72NR7 (deposit no. DSM 32563) containing 0.01 g to 10 g *Bacillus* strain is added to the following premix (per kilo of premix):

5000000 IE Vitamin A
1000000 IE Vitamin D3
13333 mg Vitamin E
1000 mg Vitamin K3
750 mg Vitamin B1
2500 mg Vitamin B2
1500 mg Vitamin B6
7666 mcg Vitamin B12
12333 mg Niacin
33333 mcg Biotin
300 mg Folic Acid
3000 mg Ca-D-Panthothenate
1666 mg Cu
16666 mg Fe
16666 mg Zn
23333 mg Mn
133 mg Co
66 mg
66 mg Se
5.8% Calcium
25% Sodium Animal Feed This is an example of an animal feed for swine comprising the animal feed additive as described above:

36.425% Barley
30.000% Wheat
12.000% Rapeseed meal
12.789% Soybean meal
5.457% Animal fat
0.975% Calcium carbonate
0.742% Monocalcium phosphate
0.408% Salt
0.096% Methionine-OH
0.609% L-lysine (50)
0.099% L-threonine
0.400% Vitamin&mineral premix The ingredients are mixed, and the feed is pelleted at the desired temperature, e.g. 60, 65, 75, 80, 85, 90 or even 95° C.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

That which is claimed:

1. A composition comprising calcium carbonate and one or more *Bacillus* strains selected from the group consisting of:
   *Bacillus licheniformis* strain O42AH3 having deposit accession number DSM 32559 and strains having all the identifying characteristics of *Bacillus licheniformis* strain DSM 32559,
   *Bacillus subtilis* strain O52YJ6 having deposit accession number DSM 32560 and strains having all the identifying characteristics of *Bacillus subtilis* strain DSM 32560,
   *Bacillus amyloliquefaciens* strain O52YYT having deposit accession number DSM 32561 and strains having all the identifying characteristics of *Bacillus amyloliquefaciens* strain DSM 32561, and
   *Bacillus pumilus* strain O72NR7 having deposit accession number DSM 32563 and strains having all the identifying characteristics of *Bacillus pumilus* strain DSM 32563.

2. The composition of claim 1, comprising *Bacillus licheniformis* strain O42AH3 having deposit accession number DSM 32559 and/or a strain having all the identifying characteristics of *Bacillus licheniformis* strain DSM 32559.

3. The composition of claim 1, comprising *Bacillus subtilis* strain O52YJ6 having deposit accession number DSM 32560 and/or a strain having all the identifying characteristics of *Bacillus subtilis* strain DSM 32560.

4. The composition of claim 1, comprising *Bacillus amyloliquefaciens* strain O52YYT having deposit accession number DSM 32561 and/or a strain having all the identifying characteristics of *Bacillus amyloliquefaciens* strain DSM 32561.

5. The composition of claim 1, comprising *Bacillus pumilus* strain O72NR7 having deposit accession number DSM 32563 and/or a strain having all the identifying characteristics of *Bacillus pumilus* strain DSM 32563.

6. The composition of claim 1, comprising at least $10^4$ colony forming units of said one or more *Bacillus* strains per gram of said composition.

7. The composition of claim 1, comprising about $10^6$ to about $10^{12}$ colony forming units of said one or more *Bacillus* strains per gram of said composition.

8. The composition of claim 1, comprising about $10^7$ to about $10^{11}$ colony forming units of said one or more *Bacillus* strains per gram of said composition.

9. A method comprising mixing the composition of claim 1 with one or more feed ingredients to produce an animal feed.

10. The method of claim 9, wherein the composition of claim 1 is mixed with said one or more feed ingredients in an amount sufficient to produce an animal feed comprising about $1\times10^{12}$ colony forming units of said one or more *Bacillus* strains per ton of animal feed.

11. An animal feed comprising the composition of claim 1.

12. The animal feed of claim 11, further comprising one or more vitamins, minerals, enzymes, amino acids, preservatives and/or antibiotics.

13. The animal feed of claim 11, comprising about $1\times10^{12}$ colony forming units of said one or more *Bacillus* strains per ton of animal feed.

14. An animal feed comprising at least one vegetable protein and one or more *Bacillus* strains selected from the group consisting of:
   *Bacillus licheniformis* strain O42AH3 having deposit accession number DSM 32559 and strains having all the identifying characteristics of *Bacillus licheniformis* strain DSM 32559,
   *Bacillus subtilis* strain O52YJ6 having deposit accession number DSM 32560 and strains having all the identifying characteristics of *Bacillus subtilis* strain DSM 32560,
   *Bacillus amyloliquefaciens* strain O52YYT having deposit accession number DSM 32561 and strains having all the identifying characteristics of *Bacillus amyloliquefaciens* strain DSM 32561, and
   *Bacillus pumilus* strain O72NR7 having deposit accession number DSM 32563 and strains having all the identifying characteristics of *Bacillus pumilus* strain DSM 32563.

15. The animal feed of claim 14, comprising *Bacillus licheniformis* strain O42AH3 having deposit accession number DSM 32559 and/or a strain having all the identifying characteristics of *Bacillus licheniformis* strain DSM 32559.

16. The animal feed of claim 14, comprising *Bacillus subtilis* strain O52YJ6 having deposit accession number DSM 32560 and/or a strain having all the identifying characteristics of *Bacillus subtilis* strain DSM 32560.

17. The animal feed of claim 14, comprising *Bacillus amyloliquefaciens* strain O52YYT having deposit accession number DSM 32561 and/or a strain having all the identifying characteristics of *Bacillus amyloliquefaciens* strain DSM 32561.

18. The animal feed of claim 14, comprising *Bacillus pumilus* strain O72NR7 having deposit accession number DSM 32563 and/or a strain having all the identifying characteristics of *Bacillus pumilus* strain DSM 32563.

19. The animal feed of claim 14, further comprising one or more vitamins, minerals, enzymes, amino acids, preservatives and/or antibiotics.

20. The animal feed of claim 14, comprising about $1\times10^{12}$ colony forming units of said one or more *Bacillus* strains per ton of said animal feed.

* * * * *

SEQUENCE LISTING

Sequence total quantity: 12
SEQ ID NO: 1    moltype = DNA    length = 1550
FEATURE         Location/Qualifiers

```
source                  1..1550
                        mol_type = genomic DNA
                        organism = Bacillus licheniformis
SEQUENCE: 1
ttagaaagga ggtgatccag ccgcaccttc cgatacggct accttgttac gacttcaccc    60
caatcatctg tcccaccttc ggcggctggc tccaaaaggt tacctcaccg acttcgggtg   120
ttacaaactc tcgtggtgtg acgggcggtg tgtacaaggc ccgggaacgt attcaccgcg   180
gcatgctgat ccgcgattac tagcgattcc agcttcacgc agtcgagttg cagactgcga   240
tccgaactga gaacagattt gtgggattgg cttagcctcg cggcttcgct gccctttgtt   300
ctgcccattg tagcacgtgt gtagcccagg tcataagggg catgatgatt tgacgtcatc   360
cccaccttcc tccggtttgt caccggcagt caccttagag tgcccaactg aatgctggca   420
actaagatca agggttgcgc tcgttgcggg acttaaccca acatctcacg cacgagctg    480
acgacaacca tgcaccacct gtcactctgc ccccgaaggg gaagccctat ctctagggtt   540
gtcagaggat gtcaagacct ggtaaggttc ttcgcgttgc ttcgaattaa accacatgct   600
ccaccgcttg tgcgggcccc cgtcaattcc tttgagtttc agtcttgcga ccgtactccc   660
caggcggagt gcttaatgcg tttgctgcag cactaaaggg cggaaccct ctaacactta   720
gcactcatcg tttacggcgt ggactaccag ggtatctaat cctgttcgct ccccacgctt   780
tcgcgcctca gcgtcagtta cagaccagag agtcgccttc gccactggtg ttcctccaca   840
tctctacgca tttcaccgct acacgtgaa ttccactctc ctcttctgca ctcaagttcc    900
ccagttccca atgaccctcc ccggttgagc cgggggcttt cacatcagac ttaagaaacc   960
gcctgcgcgc gctttacgcc caataattcc ggacaacgct tgccacctac gtattaccgc  1020
ggctgctggc acgtagttag ccgtggcttt ctggttaggt accgtcaagg tgccgcccta  1080
ttcgaacggt acttgttctt ccctaacaac agagttttac gatccgaaaa ccttcatcac  1140
tcacgcggcg ttgctccgtc agactttcgt ccattgcgga agattcccta ctgctgcctc  1200
ccgtaggagt ctgggccgtg tctcagtccc agtgtggccg atcaccctct caggtcggct  1260
acgcatcgtc gccttggtga gccgttacct caccaactag ctaatgcgcc gcgggtccat  1320
ctgtaagtgg tagctgaaag ccaccttttta tgattgaac catgcggttc aatcaagcat  1380
ccggtattag ccccggtttc ccggagttat cccagtctta caggcaggtt acccacgtgt  1440
tactcacccg tccgccgctg acctaaggga gcaagctccc gtcggtccgc tcgacttgca  1500
tgtattaggc acgccgccag cgttcgtcct gagccaggat caaactctcc             1550

SEQ ID NO: 2            moltype = DNA  length = 1555
FEATURE                 Location/Qualifiers
source                  1..1555
                        mol_type = genomic DNA
                        organism = Bacillus subtilis
SEQUENCE: 2
tttatcggag agtttgatcc tggctcagga cgaacgctgg cggcgtgcct aatacatgca    60
agtcgagcgg acagatggga gcttgctccc tgatgttagc ggcggacggg tgagtaacac   120
gtgggtaacc tgcctgtaag actgggataa ctccggaaaa ccggggctaa taccggatgg   180
ttgtttgaac cgcatggttc aaacataaaa ggtggcttcg gctaccactt acagatggac   240
ccgcggcgca ttagctagtt ggtgaggtaa cggctcacca aggcaacgat gcgtagccga   300
cctgagaggg tgatcggcca cactgggact gagacacggc ccagactcct acgggaggca   360
gcagtaggga atcttccgca atggacgaaa gtctgacgga gcaacgccgc gtgagtgatg   420
aaggttttcg gatcgtaaag ctctgttgtt agggaagaac aagtaccgtt cgaatagggc   480
ggtaccttga cggtacctaa ccagaaagcc acggctaact acgtgccagc agccgcggta   540
atacgtaggt ggcaagcgtt gtccggaatt attgggcgta aagggctcgc aggcggtttc   600
ttaagtctga tgtgaaagcc cccggctcaa ccggggaggg tcattggaaa ctggggaact   660
tgagtgcaga agaggagagt ggaattccac gtgtagcggt gaaatgcgta gagatgtgga   720
ggaacaccag tggcgaaggc gactctctgg tctgtaactg acgctgagga gcgaaagcgt   780
ggggagcgaa caggattaga taccctggta gtccacgccg taaacgatga tgtctaagtg   840
ttaggggggtt tccgcccctt agtgctgcag ctaacgcatt aagcactccg cctggggagt   900
acggtcgcaa gactgaaact caaaggaatt gacggggggcc cgcacaagcg gtggagcatg   960
tggtttaatt cgaagcaacg cgaagaacct taccaggtct tgacatcctc tgacaatcct  1020
agagatagga cgtccccttc gggggcagag tgacaggtgg tgcatggttg tcgtcagctc  1080
gtgtcgtgag atgttgggtt aagtcccgca acgagcgcaa cccttgatct tagttgccag  1140
cattcagttg ggcactctaa ggtgactgcc ggtgacaaac cggaggaagg tggggatgac  1200
gtcaaatcat catgcccctt atgacctggg ctacacacgt gctacaatgg acagaacaaa  1260
gggcagcgaa accgcgaggt taagccaatc ccacaaatct gttctcagtt cggatcgcag  1320
tctgcaactc gactgcgtga agctggaatc gctagtaatc gcggatcagc atgccgcggt  1380
gaatacgttc ccgggccttg tacacaccgc ccgtcacacc acgagagttt gtaacacccg  1440
aagtcggtga ggtaaccttt taggagccag ccgccgaagg tgggacagat gattgggtg   1500
aagtcgtaac aaggtagccg tatcggaagg tgcggctgga tcacctcctt tctaa         1555

SEQ ID NO: 3            moltype = DNA  length = 1555
FEATURE                 Location/Qualifiers
source                  1..1555
                        mol_type = genomic DNA
                        organism = Bacillus amyloliquefaciens
SEQUENCE: 3
tttatcggag agtttgatcc tggctcagga cgaacgctgg cggcgtgcct aatacatgca    60
agtcgagcgg acagatggga gcttgctccc tgatgttagc ggcggacggg tgagtaacac   120
gtgggtaacc tgcctgtaag actgggataa ctccgggaaa ccggggctaa taccggatgg   180
ttgtctgaac cgcatggttc agacataaaa ggtggcttcg gctaccactt acagatggac   240
ccgcggcgca ttagctagtt ggtgaggtaa cggctcacca aggcgacgat gcgtagccga   300
cctgagaggg tgatcggcca cactgggact gagacacggc ccagactcct acgggaggca   360
gcagtaggga atcttccgca atggacgaaa gtctgacgga gcaacgccgc gtgagtgatg   420
aaggttttcg gatcgtaaag ctctgttgtt agggaagaac aagtaccgtt caaatagggc   480
ggcaccttga cggtacctaa ccagaaagcc acggctaact acgtgccagc agccgcggta   540
```

```
atacgtaggt ggcaagcgtt gtccggaatt attgggcgta aagggctcgc aggcggtttc    600
ttaagtctga tgtgaaagcc cccgctcaa ccggggaggg tcattggaaa ctggggaact    660
tgagtgcaga agaggagagt ggaattccac gtgtagcggt gaaatgcgta gagatgtgga    720
ggaacaccag tggcgaaggc gactctctgg tctgtaactg acgctgagga gcgaaagcgt    780
ggggagcgaa caggattaga taccctggta gtccacgccg taaacgatga gtgctaagtg    840
ttaggggggtt tccgcccctt agtgctgcag ctaacgcatt aagcactccg cctggggagt    900
acggtcgcaa gactgaaact caaaggaatt gacgggggcc cgcacaagcg gtggagcatg    960
tggtttaatt cgaagcaacg cgaagaacct taccaggtct tgacatcctc tgacaatcct   1020
agagataggga cgtcccccttc ggggggcagag tgacaggtgg tgcatggttg tcgtcagctc   1080
gtgtcgtgag atgttgggtt aagtcccgca acgagcgcaa cccttgatct tagttgccag   1140
cattcagttg ggcactctaa ggtgactgcc ggtgacaaac cggaggaagg tggggatgac   1200
gtcaaatcat catgccccttt atgacctggg ctacacacgt gctacaatgg acagaacaaa   1260
gggcagcgaa accgcgaggt taagccaatc ccacaaatct gttctcagtt cggatcgcag   1320
tctgcaactc gactgcgtga agctggaatc gctagtaatc gcggatcagc atgccgcggt   1380
gaatacgttc ccgggccttg tacacaccgc ccgtcacacc acgagagttt gtaacacccg   1440
aagtcggtga ggtaacccttt taggagccag ccgccgaagg tgggacagat gattggggtg   1500
aagtcgtaac aaggtagccg tatcggaagg tgcggctgga tcacctcctt tctaa         1555

SEQ ID NO: 4            moltype = DNA   length = 1436
FEATURE                 Location/Qualifiers
source                  1..1436
                        mol_type = genomic DNA
                        organism = Bacillus pumilus
SEQUENCE: 4
agcggcggac gggtgagtaa cacgtgggta acctgcctgt aagactggga taactccggg    60
aaaccggggc taataccgga tgcttgtttg aaccgcatgg ttcaaacata aaaggtggct   120
tcggctacca cttacagatg gacccgcggc gcattagtta gttggtgagg taacggctca   180
ccaaggcaac gatgcgtagc cgacctgaga gggtgatcgg ccacactggg actgagacac   240
ggcccagact cctacgggag gcagcagtag ggaatcttcc gcaatggacg aaagtctgac   300
ggagcaacgc cgcgtgagtg atgaaggttt tcggatcgta aagctctgtt gttagggaag   360
aacaagtacc gttcgaatag ggcggtacct tgacggtacc taaccagaaa gccacgggcta   420
actacgtgcc agcagccgcg gtaatacgta ggtggcaagc gttgtccgga attattgggc   480
gtaaagggct cgcaggcggt ttcttaagtc tgatgtgaaa gccccggct caaccggggga   540
gggtcattgg aaactgggga acttgagtgc agaagaggag agtggaattc cacgtgtagc   600
ggtgaaatgc gtagagatgt ggaggaacac cagtggcgaa ggcgactctc tggtctgtaa   660
ctgacgctga ggagcgaaag cgtggggagc gaacaggatt agataccctg gtagtccacg   720
ccgtaaacga tgagtgctaa gtgttagggg gtttccgccc cttagtgctg cagctaacgc   780
attaagcact ccgcctgggg agtacggtcg caagactgaa actcaaagga attgacgggg   840
gcccgcacaa gcggtggagc atgtggttta attcgaagca acgcgaagaa ccttaccagg   900
tcttgacatc ctctgacaat cctagagata ggacgtcccc ttcggggggca gagtgacagg   960
tggtgcatgg ttgtcgtcag ctcgtgtcgt gagatgttgg gttaagtccc gcaacgagcg  1020
caaccccttga tcttagttgc cagcattcag ttgggcactc taaggtgact gccggtgaca  1080
aaccggagga aggtggggat gacgtcaaat catcatgccc cttatgacct gggctacaca  1140
cgtgctacaa tggacagaac aaagggcagc gaaaccgcga ggttaagcca atcccacaaa  1200
tctgttctca gttcggatcg cagtctgcaa ctcgactgcg tgaagctgga atcgctagta  1260
atcgcggatc agcatgccgc ggtgaatacg ttcccgggcc ttgtacacac cgcccgtcac  1320
accacgagag tttgtaacac ccgaagtcgg tgaggtaacc ttttaggagc cagccgccga  1380
aggtgggaca gatgattggg gtgaagtcgt aacaaggtag ccgtatcgga aggtgc      1436

SEQ ID NO: 5            moltype = DNA   length = 19
FEATURE                 Location/Qualifiers
misc_feature            1..19
                        note = Synthetic construct
source                  1..19
                        mol_type = other DNA
                        organism = synthetic construct
SEQUENCE: 5
gagtttgatc ctggctcag                                                   19

SEQ ID NO: 6            moltype = DNA   length = 20
FEATURE                 Location/Qualifiers
misc_feature            1..20
                        note = Synthetic construct
source                  1..20
                        mol_type = other DNA
                        organism = synthetic construct
SEQUENCE: 6
agaaaggagg tgatccagcc                                                  20

SEQ ID NO: 7            moltype = DNA   length = 21
FEATURE                 Location/Qualifiers
misc_feature            1..21
                        note = Synthetic construct
source                  1..21
                        mol_type = other DNA
                        organism = synthetic construct
SEQUENCE: 7
atctaatcct gtttgctccc c                                                21
```

-continued

```
SEQ ID NO: 8              moltype = DNA   length = 15
FEATURE                   Location/Qualifiers
misc_feature              1..15
                          note = Synthetic construct
source                    1..15
                          mol_type = other DNA
                          organism = synthetic construct
SEQUENCE: 8
tacgggaggc agcag                                                          15

SEQ ID NO: 9              moltype = DNA   length = 17
FEATURE                   Location/Qualifiers
misc_feature              1..17
                          note = Synthetic construct
source                    1..17
                          mol_type = other DNA
                          organism = synthetic construct
SEQUENCE: 9
cggtgtgtrc aaggccc                                                        17

SEQ ID NO: 10             moltype = DNA   length = 16
FEATURE                   Location/Qualifiers
misc_feature              1..16
                          note = Synthetic construct
source                    1..16
                          mol_type = other DNA
                          organism = synthetic construct
SEQUENCE: 10
caacgagcgc aaccct                                                         16

SEQ ID NO: 11             moltype = DNA   length = 1307
FEATURE                   Location/Qualifiers
source                    1..1307
                          mol_type = genomic DNA
                          organism = Bacillus subtilis
SEQUENCE: 11
tagctagttg gtgaggtaac ggctcaccaa ggcaacgatg cgtagccgac ctgagagggt    60
gatcggccac actgggactg agacacggcc cagactccta cggggaggcag cagtagggaa   120
tcttccgcaa tggacgaaag tctgacggag caacgccgcg tgagtgatga aggttttcgg    180
atcgtaaagc tctgttgtta gggaagaaca agtaccgttc gaataggcg gtaccttgac    240
ggtacctaac cagaaagcca cggctaacta cgtgccagca gccgcggtaa tacgtaggtg    300
gcaagcgttg tccggaatta ttgggcgtaa agggctcgca ggcggtttct taagtctgat    360
gtgaaagccc ccggctcaac cggggagggt cattggaaac tggggaactt gagtgcagaa    420
gaggagagtg gaattccacg tgtagcggtg aaatgcgtag agatgtggag gaacaccagt    480
ggcgaaggcg actctctggt ctgtaactga cgctgaggag cgaaagcgtg gggagcgaac    540
aggattagat accctggtag tccacgccgt aaacgatgag tgctaagtgt taggggggttt    600
ccgccccctta gtgctgcagc taacgcatta agcactccgc ctggggagta cggtcgcaag    660
actgaaactc aaaggaattg acgggggccc gcacaagcgg tggagcatgt ggtttaattc    720
gaagcaacgc gaagaacctt accaggtctt gacatcctct gacaatccta gagataggac    780
gtcccctttcg ggggcagagt gacaggtggt gcatggttgt cgtcagctcg tgtcgtgaga    840
tgttgggttta agtcccgcaa cgagcgcaac ccttgatctt agttgccagc attcagttgg    900
gcactctaag tgactgccg gtgacaaaac cggaggaaggt ggggatgacg tcaaatcatc    960
atgccccttga tgacctgggc tacacacgtg ctacaatgga cagaacaaag ggcagcgaaa    1020
ccgcgaggtt aagccaatcc cacaaatctg ttctcagttc ggatcgcagt ctgcaactcg    1080
actgcgtgaa gctggaatcg ctagtaatcg cggatcagca tgccgcggtg aatacgttcc    1140
cgggccttgt acacaccgcc cgtcacacca cgagagtttg taacacccga agtcggtgag    1200
gtaacctttt aggagccagc cgccgaaggt gggacagatg attggggtga agtcgtaaca    1260
aggtagccgt atcggaaggt gcggctggat cacctccttt ctaagga                  1307

SEQ ID NO: 12             moltype = DNA   length = 686
FEATURE                   Location/Qualifiers
source                    1..686
                          mol_type = genomic DNA
                          organism = Bacillus subtilis
SEQUENCE: 12
tttatcggag agtttgatcc tggctcagga cgaacgctgg cggcgtgcct aatacatgca     60
agtcgagcgg acagatggga gcttgctccc tgatgttagc ggcggacggg tgagtaacac    120
gtgggtaacc tgcctgtaag actgggataa ctccggaaa ccggggctaa taccggatgc    180
ttgtttgaac cgcatggttc aaacataaaa ggtggcttcg ctaccactt acagatggac    240
ccgcgcgca ttagctagtt ggtgaggtaa ggctcacca aggcaacgat gcgtagccga    300
cctgagaggg tgatcggcca cactgggact gagacacggc ccagactcct acggaggca    360
gcagtaggga atcttccgca atggacgaaa gtctgacgga gcaacgccgc gtgagtgatg    420
aaggttttcg gatcgtaaag ctctgttgtt agggaagaac aagtaccgtt cgaatagggc    480
ggtaccttga cggtacctaa ccagaaagcc acggctaact acgtgccagc agccgcggta    540
atacgtaggt ggcaagcgtt gtccggaatt attgggcgta aagggctcgc aggcggtttc    600
ttaagtctga tgtgaaagcc cccggctcaa ccggggaggt cattggaaa ctggggaact    660
tgagtgcaga gaggagagt ggaatt                                          686
```